US012342841B2

(12) United States Patent
Ayyadurai et al.

(10) Patent No.: US 12,342,841 B2
(45) Date of Patent: Jul. 1, 2025

(54) COMPOSITIONS FOR IMPROVING LOW TESTOSTERONE LEVELS

(71) Applicant: CytoSolve, Inc., Cambridge, MA (US)

(72) Inventors: V. A. Shiva Ayyadurai, Cambridge, MA (US); Prabhakar Deonikar, Cambridge, MA (US)

(73) Assignee: CytoSolve, Inc., Cambridge, MA (US)

( * ) Notice: Subject to any disclaimer, the term of this patent is extended or adjusted under 35 U.S.C. 154(b) by 101 days.

(21) Appl. No.: 17/488,195

(22) Filed: Sep. 28, 2021

(65) Prior Publication Data

US 2022/0117284 A1 Apr. 21, 2022

Related U.S. Application Data

(60) Provisional application No. 63/113,278, filed on Nov. 13, 2020, provisional application No. 63/084,326, filed on Sep. 28, 2020.

(51) Int. Cl.

| | |
|---|---|
| ***A23L 33/105*** | (2016.01) |
| ***A23L 29/00*** | (2016.01) |
| ***A23L 33/00*** | (2016.01) |
| ***A23L 33/125*** | (2016.01) |
| ***A23L 33/15*** | (2016.01) |
| ***A23L 33/175*** | (2016.01) |
| ***A61K 45/06*** | (2006.01) |
| ***A61P 5/26*** | (2006.01) |

(52) U.S. Cl.

CPC ........... *A23L 33/105* (2016.08); *A23L 29/035* (2016.08); *A23L 33/125* (2016.08); *A23L 33/15* (2016.08); *A23L 33/175* (2016.08); *A23L 33/40* (2016.08); *A61K 45/06* (2013.01); *A61P 5/26* (2018.01)

(58) Field of Classification Search

CPC .... A23L 33/105; A23L 29/035; A23L 33/175; A23L 33/125; A23L 33/15; A23L 33/40; A61P 5/26; A61K 45/06

See application file for complete search history.

(56) References Cited

U.S. PATENT DOCUMENTS 6,368,640 B1 * 4/2002 Wuh ...................... A61K 36/16 424/728

OTHER PUBLICATIONS

Krauze-Baranowska and Sowiński 2,3-Dihydrobiflavone from Ginkgo biloba Planta Med. Jun. 1999;65(5):482-4. doi: 10.1055/s-2006-960822. https://www.thieme-connect.com/products/ejournals/pdf/10.1055/s-2006-960822.pdf (Year: 1999).*

Qa'dan et al. Sci Pharm. Oct.-Dec. 2010; 78(4): 897-907.Published online Oct. 28, 2010 (Year: 2010).*

Web Page of Canadian Academy of Sports Nutrition 2016 (as evidenced by Wayback machine website) accessed Jun. 30, 2023 https://www.caasn.com/gamma-oryzanol-gh.html https://web.archive.org/web/20160801000000*/https://www.caasn.com/gamma-oryzanol-gh.html (Year: 2016).*

Barkin, Erectile dysfunction and hypogonadism (low testosterone) The Canadian Journal of Urology. 2011;18(Supplement 1):2-7 (Year: 2011).*

Neychev and Mitev The aphrodisiac herb *Tribulus terrestris* does not influence the androgen production in young men, Journal of Ethnopharmacology 101 (2005) 319-323. (Year: 2005).*

Güclü-Üstündag et al. Saponins: Properties, Applications and Processing, Critical Reviews in Food Science and Nutrition vol. 47, 2007—Issue 3 pp. 231-258. (Year: 2007).*

Liu et al. Effects of total soy saponins on free radicals in the quadriceps femoris, serum testosterone, LDH, and BUN of exhausted rats Journal of Sport and Health Science vol. 6, Issue 3, Sep. 2017, pp. 359-364 (Year: 2017).*

Ayyadurai and Deonikar, "Do GMOs Accumulate Formaldehyde and Disrupt Molecular Systems Equilibria? Systems Biology May Provide Answers", Agricultural Sciences, Jul. 10, 2015; 6:630-662.

Ayyadurai and Dewey, "CytoSolve: A Scalable Computational Method for Dynamic Integration of Multiple Molecular Pathway Models", Cellular and Molecular Bioengineering, Mar. 2011, 4(1):28-45.

Ayyadurai, "Scalable Computational Architecture for Integrating Biological Pathway Models", Doctoral Dissertation Massachusetts Institute of Technology, Aug. 2007, 321 pages.

Ayyadurai, "Services-Based Systems Architecture for Modeling the Whole Cell: A Distributed Collaborative Engineering Systems Approach", Commun Med Care Compunetics, 2011, 1:115-168.

Bekaert et al., "Determinants of testosterone levels in human male obesity", Endocrine, Mar. 13, 2015, 50(1): 202-211.

Dhindsa et al., "Low Estradiol Concentrations in Men With Subnormal Testosterone Concentrations and Type 2 Diabetes", Diabetes Care. Aug. 2011, 34(8): 1854-1859.

Koo et al., "In silico modeling of shear-stress-induced nitric oxide production in endothelial cells through systems biology", Biophys J., May 2013, 104(10):2295-306.

Leisegang et al., "The in vitro modulation of steroidogenesis by inflammatory cytokines and insulin in TM3 Leydig cells", Reprod Biol Endocrinol, Mar. 22, 2018, 11 pages.

Nordsletten et al., "Multiscale mathematical modeling to support drug development", IEEE Trans BiomedEng, Oct. 24, 2011, 58(12):3508-12.

Patel et al., "Effects of metformin and leuprolide acetate on insulin resistance and testosterone levels in nondiabetic postmenopausal women: a randomized, placebo-controlled trial", Fertil. Steril, Nov. 1, 2010, 94(6): 2161-2166.

Sweeney et al., "Pericytes of the neurovascular unit: key functions and signaling pathways," Nat Neurosci, Jun. 2016; 19(6):771-83.

* cited by examiner

*Primary Examiner* — Amanda L. Aguirre
*Assistant Examiner* — William Y Lee
(74) *Attorney, Agent, or Firm* — Oblon, McClelland, Maier & Neustadt, L.L.P.

(57) ABSTRACT

The present disclosure is related to dietary supplements. In some aspects, this disclosure relates to compositions that can include, one or more agents that can increase the synthesis of testosterone, decrease the degradation of testosterone, and/or decrease the oxidative stress. In some embodiments, an agent of the composition includes: a mineral, a carboxylic acid, a flavone, a flavan, a terpinoid, an amino acid, a benzopyran; and a glycoside, and a combination thereof.

3 Claims, 2 Drawing Sheets

COMPOSITIONS FOR IMPROVING LOW TESTOSTERONE LEVELS

CROSS-REFERENCE TO RELATED APPLICATIONS

This application claims the benefit of U.S. Provisional Application No. 63/113,278, filed Nov. 13, 2020 and U.S. Provisional Application No. 63/084,326, filed Sep. 28, 2020, the contents of which are hereby incorporated by reference.

TECHNICAL FIELD

This disclosure is related to the field of dietary supplements. For example, this disclosure relates to compositions useful for improving low testosterone levels. Such compositions can include, for example, one or more agents that increase the concentration of testosterone, decreases testosterone degradation, and/or decrease reactive oxygen species (ROS) production.

BACKGROUND

Testosterone levels generally peak during adolescence and early adulthood. A reduction of 0.4-2% annually is observed in adults more than 30 years old naturally. However, low testosterone (Low T) levels caused by male hypogonadism results in poor cardiovascular health. Baltimore Longitudinal Study of Aging (BLSA) reported that approximately 12, 20, 30, and 50% of men in their 50s, 60s, 70s, and 80s, respectively, are hypogonadal. Additionally, higher body mass index and/or type II diabetes mellitus may be associated with lower circulating testosterone levels. Low T arising from hypogonadism leads to decreased libido, erectile dysfunction, depression or anxiety, reduced muscle mass, less energy, weight gain, and anemia. In the United States, it is estimated that hypogonadism affects up to 4 million men.

Currently, there are many treatments recommended for improving Low T levels. For example, testosterone replacement therapy (TRT). Although TRT can increase testosterone levels and improve libido, the improvements are less robust and short lived. In addition, some joint stiffness, inflammation, and pain, TRT can also lead to side-effects such as polycythemia, peripheral edema, cardiac and hepatic dysfunction. Methods and compositions for improving free testosterone levels are highly desirable.

SUMMARY

Provided herein are methods for improving Low T in a subject in need thereof comprising administering to the subject a composition comprising two or more agents that increase free testosterone concentrations.

In some embodiments, Low T is associated with one or more of: an injury, infection, cancer chemotherapy, sarcoidosis, obstructive sleep apnea chronic illnesses such as hyperthyroidism, renal failure and cirrhosis, alcoholism, obesity, stress, diabetes mellitus, or aging.

In some embodiments, at least one agent that increases the concentration of free testosterone also decreases testosterone degradation and decreases reactive oxygen species (ROS) concentration; or a combination thereof.

In some embodiments, at least one agent that increases the concentration of free testosterone modulates testosterone synthesis and cholesterol uptake pathway. In some embodiments, at least one agent that decreases the testosterone degradation modulates testosterone degradation pathway. In some embodiments, at least one agent that decreases the concentration of ROS modulates oxidative stress pathway.

In some embodiments, the two or more agents that increase concentration of free testosterone comprise one or more of: a mineral; a carboxylic acid; a flavone; a flavan; a terpinoid; an amino acid; a benzopyran; and, a glycoside.

Also provided herein are methods for improving Low T in a subject in need thereof comprising administering to the subject a composition comprising two or more agents that increase the concentration of testosterone, decrease the degradation of testosterone; decrease the concentration of ROS; or a combination thereof.

In some embodiments, Low T is associated with one or more of: an injury, infection, cancer chemotherapy, sarcoidosis, obstructive sleep apnea chronic illnesses such as hyperthyroidism, renal failure and cirrhosis, alcoholism, obesity, stress, diabetes mellitus, or aging.

In some of any of the above embodiments, the mineral is an elemental metal. In some embodiments, the mineral is selected from the group consisting of: manganese, calcium, magnesium, zinc, iron, selenium, and a combination thereof.

In some embodiments, the mineral is zinc.

In some embodiments, the mineral is present in an amount of about 1% to about 30% w/w of the composition. In some embodiments, the mineral is present in an amount of about 2% to about 20% w/w of the composition. In some embodiments, the mineral is present in an amount of about 3% to about 15% w/w of the composition. In some embodiments, the mineral is present in an amount of about 9.1% w/w of the composition.

In some of any of the above embodiments, the carboxylic acid is a cinnamate. In some embodiments, the carboxylic acid is selected from the group consisting of: picroside II, clocinnamox, hydrocinnamic acid, rosmarinic acid, caffeic acid, and a combination thereof.

In some embodiments, the carboxylic acid is caffeic acid.

In some embodiments, the carboxylic acid is present in an amount of about 0.5% to about 20% w/w of the composition. In some embodiments, the carboxylic acid is present in an amount of about 1% to about 15% w/w of the composition. In some embodiments, the carboxylic acid is present in an amount of about 2% to about 10% w/w of the composition. In some embodiments, the carboxylic acid is present in an amount of about 4.7% w/w of the composition.

In some of any of the above embodiments, the carboxylic acid is a ketoaldonic acid. In some embodiments, the carboxylic acid is selected from the group consisting of: D or L-ascorbic acid (vitamin C), erythorbic acid, gulonic acid, and a combination thereof.

In some embodiments, the carboxylic acid is vitamin C.

In some embodiments, the carboxylic acid is present in an amount of about 0.5% to about 20% w/w of the composition. In some embodiments, the carboxylic acid is present in an amount of about 1% to about 15% w/w of the composition. In some embodiments, the carboxylic acid is present in an amount of about 2% to about 10% w/w of the composition. In some embodiments, the carboxylic acid is present in an amount of about 4.6% w/w of the composition.

In some of any of the above embodiments, the flavone is a pentahydroxyflavone. In some embodiments, the flavone is selected from the group consisting of: quercetin, luteolin, and a combination thereof.

In some embodiments, the flavone is quercetin.

In some embodiments, the flavone is present in an amount of about 0.5% to about 25% w/w of the composition. In some embodiments, the flavone is present in an amount of about 1% to about 20% w/w of the composition. In some embodiments, the flavone is present in an amount of about 2% to about 15% w/w of the composition. In some embodiments, the flavone is present in an amount of about 5.9% w/w of the composition.

In some of any of the above embodiments, the flavone is a tetrahydroxyflavone. In some embodiments, the flavone is selected from the group consisting of: nigrasin I, rutin, macaranone B, avicularin, and a combination thereof.

In some embodiments, the flavone is rutin.

In some embodiments, the flavone is present in an amount of about 0.5% to about 25% w/w of the composition. In some embodiments, the flavone is present in an amount of about 1% to about 15% w/w of the composition. In some embodiments, the flavone is present in an amount of about 1.5% to about 5% w/w of the composition. In some embodiments, the flavone is present in an amount of about 2.9% w/w of the composition.

In some embodiments, the flavone is a trihydroxyflavone. In some embodiments, the flavone is selected from the group consisting of: apigenin, baicalein, norwogonin, galangin, and a combination thereof.

In some embodiments, the flavone is apigenin.

In some embodiments, the flavone is present in an amount of about 0.01% to about 5% w/w of the composition. In some embodiments, the flavone is present in an amount of about 0.05% to about 2% w/w of the composition. In some embodiments, the flavone is present in an amount of about 0.1% to about 1% w/w of the composition. In some embodiments, the flavone is present in an amount of about 0.7% w/w of the composition.

In some embodiments, the flavone is a flavanol. In some embodiments, the flavone is selected from the group consisting of: myrcetin, icariin, sexangularetin, kaempferol, isorhamnetin, and a combination thereof.

In some embodiments, the flavone is icariin.

In some embodiments, the flavone is present in an amount of about 0.05% to about 15% w/w of the composition. In some embodiments, the flavone is present in an amount of about 0.1% to about 10% w/w of the composition. In some embodiments, the flavone is present in an amount of about 0.5% to about 5% w/w of the composition. In some embodiments, the flavone is present in an amount of about 1.3% w/w of the composition.

In some embodiments, the flavone is a flavanol. In some embodiments, the flavone is selected from the group consisting of: myrcetin, icariin, sexangularetin, kaempferol, isorhamnetin, and a combination thereof.

In some embodiments, the flavone is kaempferol.

In some embodiments, the flavone is present in an amount of about 0.025% to about 2% w/w of the composition. In some embodiments, the flavone is present in an amount of about 0.05% to about 1% w/w of the composition. In some embodiments, the flavone is present in an amount of about 0.075% to about 0.2% w/w of the composition. In some embodiments, the flavone is present in an amount of about 0.1% w/w of the composition.

In some embodiments, the flavan is a flavan 3-ol. In some embodiments, the flavan is selected from the group consisting of: epicatechin, catechin, epigallocatechin, fisetinidol, (−)-epigallocatechin gallate (EGCG), and a combination thereof.

In some embodiments, the flavan is epicatechin.

In some embodiments, the flavan is present in an amount of about 0.025% to about 2% w/w of the composition. In some embodiments, the flavan is present in an amount of about 0.05% to about 1.5% w/w of the composition. In some embodiments, the flavan is present in an amount of about 0.1% to about 1% w/w of the composition. In some embodiments, the flavan is present in an amount of about 0.3% w/w of the composition.

In some embodiments, the flavan is a flavan 3-ols. In some embodiments, the flavan is selected from the group consisting of: epicatechin, catechin, epigallocatechin, fisetinidol, EGCG, and a combination thereof.

In some embodiments, the flavan is EGCG.

In some embodiments, the flavan is present in an amount of about 0.5% to about 25% w/w of the composition. In some embodiments, the flavan is present in an amount of about 1% to about 20% w/w of the composition. In some embodiments, the flavan is present in an amount of about 2% to about 10% w/w of the composition. In some embodiments, the flavan is present in an amount of about 8% w/w of the composition.

In some embodiments, the terpenoid is a triterpenoid. In some embodiments, the terpenoid is selected from the group consisting of: hypodiol, tubeimoside, gamma oryzanol, and a combination thereof.

In some embodiments, the terpenoid is gamma oryzanol.

In some embodiments, the terpenoid is present in an amount of about 1% to about 70% w/w of the composition. In some embodiments, the terpenoid is present in an amount of about 5% to about 50% w/w of the composition. In some embodiments, the terpenoid is present in an amount of about 15% to about 35% w/w of the composition. In some embodiments, the terpenoid is present in an amount of about 21.7% w/w of the composition.

In some embodiments, the amino acid is an α-amino acid. In some embodiments, the amino acid is selected from the group consisting of: D-glutamine, L-glutamine, L-alanine, D-alanine, D-cycloserine, N-methylglycine, L-serine, D-serine, N,N,N-trimethylglycine, 3-amino-1-hydroxypyrrolid-2-one, (R)—(N-[3-(4'-fluorophenyl)-3-{4'-phenylphenoxy) propyl]) sarcosine, N-methyl-N-[3-[(4-trilfluoromethyl) phenoxy]-3-phenyl-propyl]glycine, D-aspartic acid and a combination thereof.

In some embodiments, the amino acid is D-aspartic acid.

In some embodiments, the amino acid is present in an amount of about 1% to about 70% w/w of the composition. In some embodiments, the amino acid is present in an amount of about 5% to about 50% w/w of the composition. In some embodiments, the amino acid is present in an amount of about 15% to about 35% w/w of the composition. In some embodiments, the amino acid is present in an amount of about 21.7% w/w of the composition.

In some embodiments, the benzopyran is a chromanol. In some embodiments, the benzopyran is selected from the group consisting of: α-tocopherol, β-tocopherol, γ-tocopherol, δ-tocopherol, α-tocotrienol, β-tocotrienol, γ-tocotrienol, δ-tocotrienol, and a combination thereof.

In some embodiments, benzopyran is a combination of α-tocopherol, β-tocopherol, γ-tocopherol, and δ-tocopherol (vitamin E).

In some embodiments, the benzopyran is present in an amount of about 1% to about 30% w/w of the composition. In some embodiments, the benzopyran is present in an amount of about 3% to about 20% w/w of the composition. In some embodiments, the benzopyran is present in an amount of about 6% to about 15% w/w of the composition. In some embodiments, the benzopyran is present in an amount of about 11.6% w/w of the composition.

In some embodiments, the glycoside is selected from the group consisting of: saponin, ginsenoside Rg1, ligustroside, and a combination thereof.

In some embodiments, the glycoside is saponin.

In some embodiments, the glycoside is present in an amount of about 1% to about 30% w/w of the composition. In some embodiments, the glycoside is present in an amount of about 2% to about 20% w/w of the composition. In some embodiments, the glycoside is present in an amount of about 3% to about 10% w/w of the composition. In some embodiments, the glycoside is present in an amount of about 7.4% w/w of the composition.

In some embodiments, the mineral is zinc; the carboxylic acid is caffeic acid and/or vitamin C (ascorbic acid); the flavon is quercetin, rutin, apigenin, icariin, and/or kaempferol; the flavan is epicatechin and/or EGCG; the terpenoid is gamma oryzanol; the amino acid is D-aspartic acid; the benzopyran is vitamin E; and, the glycoside is saponin.

In some embodiments, the composition comprises two or more of: zinc; caffeic acid; vitamin C; quercetin; rutin; apigenin; icariin; kaempferol; epicatechin; EGCG; gamma oryzanol; D-aspartic acid; vitamin E; and, saponin. In some embodiments, the composition comprises three or more of: zinc; caffeic acid; vitamin C; quercetin; rutin; apigenin; icariin; kaempferol; epicatechin; EGCG; gamma oryzanol; D-aspartic acid; vitamin E; and, saponin. In some embodiments, the composition comprises four or more of: zinc; caffeic acid; vitamin C; quercetin; rutin; apigenin; icariin; kaempferol; epicatechin; EGCG; gamma oryzanol; D-aspartic acid; vitamin E; and, saponin. In some embodiments, the composition comprises five or more of: zinc; caffeic acid; vitamin C; quercetin; rutin; apigenin; icariin; kaempferol; epicatechin; EGCG; gamma oryzanol; D-aspartic acid; vitamin E; and, saponin. In some embodiments, the composition comprises six or more of: zinc; caffeic acid; vitamin C; quercetin; rutin; apigenin; icariin; kaempferol; epicatechin; EGCG; gamma oryzanol; D-aspartic acid; vitamin E; and, saponin. In some embodiments, the composition comprises seven or more of: zinc; caffeic acid; vitamin C; quercetin; rutin; apigenin; icariin; kaempferol; epicatechin; EGCG; gamma oryzanol; D-aspartic acid; vitamin E; and, saponin. In some embodiments, the composition comprises eight or more of: zinc; caffeic acid; vitamin C; quercetin; rutin; apigenin; icariin; kaempferol; epicatechin; EGCG; gamma oryzanol; D-aspartic acid; vitamin E; and, saponin. In some embodiments, the composition comprises nine or more of: zinc; caffeic acid; vitamin C; quercetin; rutin; apigenin; icariin; kaempferol; epicatechin; EGCG; gamma oryzanol; D-aspartic acid; vitamin E; and, saponin. In some embodiments, the composition comprises ten or more of: zinc; caffeic acid; vitamin C; quercetin; rutin; apigenin; icariin; kaempferol; epicatechin; EGCG; gamma oryzanol; D-aspartic acid; vitamin E; and, saponin. In some embodiments, the composition comprises eleven or more of: zinc; caffeic acid; vitamin C; quercetin; rutin; apigenin; icariin; kaempferol; epicatechin; EGCG; gamma oryzanol; D-aspartic acid; vitamin E; and, saponin. In some embodiments, the composition comprises twelve or more of: zinc; caffeic acid; vitamin C; quercetin; rutin; apigenin; icariin; kaempferol; epicatechin; EGCG; gamma oryzanol; D-aspartic acid; vitamin E; and, saponin. In some embodiments, the composition comprises thirteen or more of: zinc; caffeic acid; vitamin C; quercetin; rutin; apigenin; icariin; kaempferol; epicatechin; EGCG; gamma oryzanol; D-aspartic acid; vitamin E; and, saponin.

In some embodiments, the composition comprises: zinc present in an amount of about 3% to about 15% w/w of the composition; caffeic acid present in an amount of about 2% to about 10% w/w of the composition; vitamin C present in an amount of about 2% to about 10% w/w of the composition; quercetin present in an amount of about 2% to about 15% w/w of the composition; rutin present in an amount of about 1.5% to about 5% w/w of the composition; apigenin present in an amount of about 0.1% to about 1% w/w of the composition; icariin present in an amount of about 0.5% to about 5% w/w of the composition; kaempferol present in an amount of about 0.075% to about 0.2% w/w of the composition; epicatechin present in an amount of about 0.1% to about 1% w/w of the composition; EGCG present in an amount of about 2% to about 10% w/w of the composition; gamma oryzanol present in an amount of about 15% to about 35% w/w of the composition; D-aspartic acid present in an amount of about 15% to about 35% w/w of the composition; vitamin E present in an amount of about 6% to about 15% w/w of the composition; and, saponin present in an amount of about 3% to about 10% w/w of the composition.

In some embodiments, the composition comprises: zinc present in an amount of about 9.1% w/w of the composition; caffeic acid is present in an amount of about 4.7% w/w of the composition; vitamin C is present in an amount of about 4.6% w/w of the composition; quercetin is present in an amount of about 5.9% w/w of the composition; rutin is present in an amount of about 2.9% w/w of the composition; apigenin is present in an amount of about 0.7% w/w of the composition; icariin is present in an amount of about 1.3% w/w of the composition; kaempferol is present in an amount of about 0.1% w/w of the composition; epicatechin is present in an amount of about 0.3% w/w of the composition; EGCG is present in an amount of about 8% w/w of the composition; gamma oryzanol is present in an amount of about 21.7% w/w of the composition; D-aspartic acid is present in an amount of about 21.7% w/w of the composition; vitamin E is present in an amount of about 11.6% w/w of the composition; and, saponin is present in an amount of about 7.4% w/w of the composition.

In some embodiments, the composition further comprises one or more excipients, diluents, or carriers.

In some embodiments, the composition is administered orally.

In some embodiments, the composition is a configured as a powder.

Also provided herein is a method for improving and/or stabilizing the free testosterone concentration of a subject comprising administering to the subject a composition as described herein.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
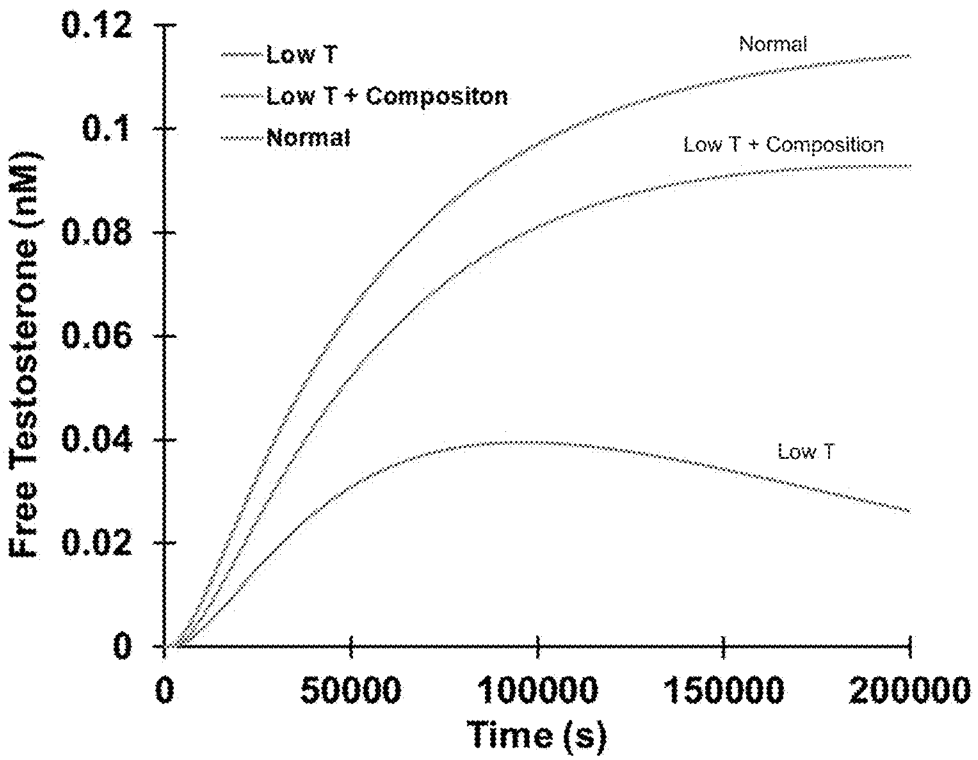
FIG. 1 is a rate curve comparing the concentration of free testosterone levels for normal individuals, individuals with Low T without supplementation of composition described herein, and individuals with Low T with supplementation of composition described herein, over a period of 2 days. The plot is based on a biomolecular computational model using CytoSolve® and modeling mechanisms of the testosterone synthesis, testosterone degradation, and oxidative stress.

Testosterone is an important male sex hormone that regulates various biological functions including increasing bone strength and density, inducing hematopoiesis, driving sexual function and libido, providing a cardioprotective effect and increasing muscle strength. Testosterone levels generally peak during adolescence and early adulthood. A reduction of 0.4-2% annually is observed in adults more than 30 years old naturally. However, low testosterone (Low T) levels caused by male hypogonadism results in poor cardiovascular health. Additionally, higher body mass index and/or type II diabetes mellitus may be associated with lower circulating testosterone levels. Low T arising from hypogonadism leads to decreased libido, erectile dysfunction, depression or anxiety, reduced muscle mass, less energy, weight gain, and anemia.

Testosterone replacement therapy (TRT) is a widely used treatment for improving Low T levels by increasing free testosterone levels directly. Although TRT can increase testosterone levels and improve libido, the improvements are less robust and short lived. In addition to some joint stiffness, inflammation, and pain, TRT can also lead to side-effects such as polycythemia, peripheral edema, cardiac and hepatic dysfunction. On the other hand, the compositions as described herein mitigate Low T via three different mechanisms of action involved in regulation of testosterone metabolism including upregulation of synthesis of testosterone, downregulation of testosterone degradation, and downregulation of oxidative stress.

Accordingly, the present disclosure provides methods and compositions (e.g., dietary supplements) related to improvement of Low T. Such compositions can contain two or more agents that increase testosterone synthesis, decrease the degradation of testosterone, and lower oxidative stress, or a combination thereof, useful for improvement in free testosterone concentrations.

Definitions

As used herein, the phrase "Low T" or "low concentrations of testosterone" a disease, disorder, or condition encompasses a subject with lower concentrations of free testosterone that has also been diagnosed with, was previously diagnosed with, or has symptoms associated with the disease, disorder, or condition.

As used herein, the phrases an "effective amount" or a "therapeutically effective amount" of an active agent or ingredient, or pharmaceutically active agent or ingredient, refer to an amount of the active agent sufficient enough to reduce or eliminate one or more symptoms of the disorder or to effect a cure upon administration. Effective amounts of the active agent will vary with the kind of active agent chosen, the particular condition or conditions being treated, the severity of the condition, the duration of the treatment, the specific components of the composition being used, and like factors.

As used herein, "subject" refers to any subject, particularly a mammalian subject, for whom diagnosis, prognosis, or therapy is desired, for example, a human.

Reference to the term "about" has its usual meaning in the context of compositions to allow for reasonable variations in amounts that can achieve the same effect and also refers herein to a value of plus or minus 10% of the provided value. For example, "about 20" means or includes amounts from 18 to and including 22.

As used herein, a "treatment" or "treating" of a disease, disorder, or condition encompasses alleviation of at least one symptom thereof, a reduction in the severity thereof, or the delay or inhibition of the progression thereof. Treatment need not mean that the disease, disorder, or condition is totally cured. A useful composition herein needs only to reduce the severity of a disease, disorder, or condition, reduce the severity of one or more symptoms associated therewith, or provide improvement to a patient or subject's quality of life.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. As used herein, the singular form "a", "an", and "the" include plural references unless indicated otherwise. For example, "an" excipient includes one or more excipients. It is understood that aspects and variations of the invention described herein include "consisting of" and/or "consisting essentially of" aspects and variations.

Agents that Increase the Concentration of Free Testosterone

In some embodiments, a composition as described herein can comprise an agent that increases the concentration of free testosterone. For example, in some embodiments, an agent that can increase the concentration of free testosterone is an agent that can increase the synthesis of testosterone. As another example, an agent that can increase the concentration of free testosterone can be an agent that can decrease a degradation of testosterone, and can decrease oxidative stress. Many agents that increase the concentration of free testosterone are known to one of skill in the art. Non-limiting examples of an agent that increases the concentration of free testosterone include zinc, caffeic acid, vitamin C, quercetin, rutin, apigenin, icariin, kaempferol, epicatechin, EGCG, gamma oryzanol, D-aspartic acid, vitamin E, and saponin. Several methods for measuring free testosterone concentration are known to one of ordinary skill in the art. Non-limiting examples of such methods include: measuring free testosterone concentration using "equilibrium dialysis" technique (see, for example, Bekaert et al. *Endocrine.* 2015 Mar. 13, 50(1): 202-211; Patel et al. *Fertil. Steril.* 2010 November; 94(6): 2161-2166; and Dhindsa et al. *Diabetes Care.* 2011 August; 34(8): 1854-1859; each of which are incorporated by reference herein in their entireties).

In some embodiments, an agent that increases the concentration of free testosterone by at least 0.5%, 1%, 5%, 10%, or 15%. For example, the agent that can increase the concentration of free testosterone can increase the concentration of free testosterone by about 1%, about 2%, about 3%, about 4%, about 5%, about 10%, about 15% or more.

Minerals

In some embodiments, a composition as described herein includes a mineral that modulates testosterone concentration. In some embodiments, a composition as described herein includes a mineral that increases the synthesis testosterone. In some embodiments, a composition as described herein includes a mineral that decreases testosterone degradation. In some embodiments, a composition as described herein includes a mineral that decreases oxidative stress.

As described herein, a "mineral" refers to an elemental atom and their salts.

Non-limiting examples of minerals include metals and non-metals. Examples of a metals include, without limitation, manganese, calcium, magnesium, zinc, iron, selenium. Non-limiting examples of minerals that can increase testosterone concentration include zinc.

Carboxylic Acids

In some embodiments, a composition as described herein includes a carboxylic acid that modulates testosterone concentration. In some embodiments, a composition as described herein includes a carboxylic acid that increases the synthesis testosterone. In some embodiments, a composition as described herein includes a carboxylic acid that decreases testosterone degradation. In some embodiments, a composition as described herein includes a carboxylic acid that decreases oxidative stress.

As described herein a "carboxylic acid" refers to a compound containing a —COOH.

Non-limiting examples of a carboxylic acid include cinnamate and ketoaldonic acid. Examples of a cinnamate include, without limitation, picroside II, clocinnamox, hydrocinnamic acid, rosmarinic acid, and caffeic acid. Examples of ketoaldonic acid include, without limitation, D- or L-ascorbic acid (vitamin C), erythorbic acid, and gulonic acid. Non-limiting examples of carboxylic acids that can increase testosterone concentration include caffeic acid and vitamin C.

Flavones

In some embodiments, a composition as described herein includes a flavone that modulates testosterone concentration. In some embodiments, a composition as described herein includes a flavone that increases the synthesis testosterone. In some embodiments, a composition as described herein includes a flavone that decreases testosterone degradation. In some embodiments, a composition as described herein includes a flavone that decreases oxidative stress.

As described herein, a "flavone" refers to a molecule derived from the oxidation of a flavan to form a phenylbenzopyranone motif.

Non-limiting examples of flavones include pentahydroxyflavones, tetrahydroxyflavones, trihydroxyflavones, hydroxyflavones, and flavanols. Examples of a pentahydroxyflavone include, without limitation, quercetin and luteolin. Examples of a tetrahydroxyflavone include, without limitation, nigrasin I, rutin, macaranone B, and avicularin. Examples of a trihydroxyflavone include, without limitation, apigenin, baicalein, norwogonin, and galangin. Examples of a flavonols include, without limitation, myrcetin, icariin, sexangularetin, kaempferol, and isorhamnetin. Non-limiting examples of flavones that can increase testosterone concentration include apigenin, rutin, quercetin, kaempferol, and icariin.

Flavans

In some embodiments, a composition as described herein includes a flavan that modulates testosterone concentration. In some embodiments, a composition as described herein includes a flavan that increases the synthesis testosterone. In some embodiments, a composition as described herein includes a flavan that decreases testosterone degradation. In some embodiments, a composition as described herein includes a flavan that decreases oxidative stress.

As described herein, a "flavan" refers to a molecule derived from benzopyran that use the 2-phenyl-3,4-dihydro-2H-chromene skeleton.

Non-limiting examples of flavans include flavan-3-ols, flavan-4-ols and flavan-3,4-diols. Examples of a flavan-3-ols include, without limitation, epicatechin, catechin, epigallocatechin, fisetinidol, EGCG. Non-limiting examples of flavans that can increase testosterone concentration include epicatechin and EGCG.

Terpenoids

In some embodiments, a composition as described herein includes a terpenoid that modulates testosterone concentration. In some embodiments, a composition as described herein includes a terpenoid that increases the synthesis testosterone. In some embodiments, a composition as described herein includes a terpenoid that decreases testosterone degradation. In some embodiments, a composition as described herein includes a terpenoid that decreases oxidative stress.

A "terpenoid" refers to a molecule derived from the modification (e.g., oxidation) of a terpene. Many terpenoids are derived biosynthetically from units of isoprene.

Non-limiting examples of a terpenoid include monoterpenes, diterpenes, triterpenes, hemiterpenes, sesquiterpenes, sesterterpenes, sesquarterpenes, and notisoprenoids. Examples of a triterpines, without limitation, include hypodiol, tubeimoside, and gamma oryzanol. Non-limiting examples of terpenoid that can increase testosterone concentration include gamma oryzanol.

Amino Acids

In some embodiments, a composition as described herein includes an amino acid that modulates testosterone concentration. In some embodiments, a composition as described herein includes an amino acid that increases the synthesis testosterone. In some embodiments, a composition as described herein includes an amino acid that decreases testosterone degradation.

As described herein, an "amino acid" refers to naturally and non-naturally occurring L- and D-amino acids, peptidomimetic amino acids, and non-standard amino acids that are not made by a standard machinery or are only found in proteins after post-translational modification or as metabolic intermediates.

In some embodiments, the amino acid is an $\alpha$-amino acid. Non-limiting examples of $\alpha$-amino acids include, but are not limited to, D-glutamine, L-glutamine, L-alanine, D-alanine, D-cycloserine, N-methylglycine, L-serine, D-serine, N,N,N-trimethylglycine, 3-amino-1-hydroxypyrrolid-2-one, (R)—(N-[3-(4'-fluorophenyl)-3-{4'-phenylphenoxy)propyl]) sarcosine, N-methyl-N-[3-[(4-trilfluoromethyl)phenoxy]-3-phenyl-propyl]glycine, and D-aspartic acid. Non-limiting examples of amino acids that can increase concentration testosterone include D-aspartic acid.

Benzopyrans

In some embodiments, a composition as described herein includes a benzopyran that modulates testosterone concentration. In some embodiments, a composition as described herein includes a benzopyran that increases the synthesis testosterone. In some embodiments, a composition as described herein includes a benzopyran that decreases testosterone degradation. In some embodiments, a composition as described herein includes a benzopyran that decreases oxidative stress.

As described herein, a "benzopyran" refers to a polycyclic organic compound comprising a benzene ring fused to a pyran ring.

Non-limiting examples of benzopyran include chromonols. Examples of a chromonols include, without limitation, α-tocopherol, β-tocopherol, γ-tocopherol, and δ-tocopherol (vitamin E). Non-limiting examples of benzopyran that can increase testosterone concentration include α-tocopherol, β-tocopherol, γ-tocopherol, and δ-tocopherol (vitamin E).

Glycoside

In some embodiments, a composition as described herein includes a glycoside that modulates testosterone concentration. In some embodiments, a composition as described herein includes a glycoside that increases the synthesis testosterone. In some embodiments, a composition as described herein includes a glycoside that decreases testosterone degradation. In some embodiments, a composition as described herein includes a glycoside that decreases oxidative stress.

As described herein, a "glycoside" refers to a polycyclic organic compound comprising a sugar molecule bound to another functional group such as a terpene or a steroid via a glycosidic bond.

Examples of a glycoside include, without limitation, saponin, ginsenoside Rg1, and ligustroside. Non-limiting examples of glycosides that can increase testosterone concentration include saponin, ginsenoside Rg1, and ligustroside.

Dietary Supplemental Compositions

The present disclosure provides compositions (e.g., dietary supplements) containing two or more agents that increase the synthesis of testosterone, decrease the degradation of testosterone, decrease the oxidative stress, or a combination thereof. For example, in some embodiments, the present disclosure provides a compositions comprising two or more agents that increase the synthesis of testosterone. As another example, in some embodiments, the present disclosure provides a composition comprising two or more agents that decrease the degradation of testosterone; decrease the oxidative stress; or a combination thereof. In some embodiments, the present disclosure provides compositions comprising a mineral, a carboxylic acid, a flavone, a flavan, a terpinoid, an amino acid, a benzopyran, and a glycoside. Such compositions can be used to increase the free testosterone concentrations. In addition, the disclosure provides methods for relieving symptoms caused by Low T associated with one or more of: an injury, infection, cancer chemotherapy, sarcoidosis, obstructive sleep apnea chronic illnesses such as hyperthyroidism, renal failure and cirrhosis, alcoholism, obesity, stress, diabetes mellitus, or aging. Such methods involve the administration of a composition as provided herein.

In some embodiments, a composition as described herein includes two or more agents that increase the synthesis of testosterone. In some embodiments, at least one of the agents that increases the synthesis of testosterone also decreases degradation of testosterone. In some embodiments, at least one of the agents that increases the synthesis of testosterone also decreases oxidative stress. In some embodiments, the two or more agents that increase testosterone synthesis include a mineral, a carboxylic acid, a flavone, a flavan, a terpinoid, an amino acid, a benzopyran, and a glycoside.

In some embodiments, a composition as described herein includes a mineral that can modulate testosterone synthesis. In some embodiments, a composition as described herein includes a mineral that decreases testosterone degradation. In some embodiments, a composition as described herein includes a mineral that decreases oxidative stress.

In some embodiments, a mineral is present in an amount of about 1% to about 30% w/w of the composition. For example, about 1% to about 5%, about 1% to about 10%, about 1% to about 15%, about 1% to about 20%, about 1% to about 25%, about 25% to about 30%, about 20% to about 30%, about 15% to about 30%, about 10% to about 30%, about 5% to about 30%, about 5% to about 29%, or about 15% to about 29% w/w of the composition. In some embodiments, the mineral is present in an amount of about 5% to about 15% w/w of the composition. For example, about 5% to about 6%, about 5% to about 7%, about 5% to about 8%, about 5% to about 9%, about 5% to about 10%, about 5% to about 11%, about 5% to about 12%, about 5% to about 13%, about 5% to about 14%, about 14% to about 15%, about 13% to about 15%, about 12% to about 15%, about 11% to about 15%, about 10% to about 15%, about 8% to about 15%, about 7% to about 15%, or about 6% to about 15% w/w of the composition. In some embodiments, the mineral is present in an amount of about 5%, about 5.5%, about 6%, about 6.5%, about 7%, about 7.5%, about 8%, about 8.5%, about 9%, about 9.1%, about 9.5%, about 10%, about 10.5%, about 11%, about 11.5%, about 12%, about 12.5%, about 13%, about 13.5%, about 14%, about 14.5%, or about 15% w/w of the composition.

In some embodiments, the mineral is an elemental metal. In some embodiments, the elemental metal is selected from the group consisting of: manganese, calcium, magnesium, zinc, iron, selenium, and a combination thereof.

In some embodiments, the mineral is zinc. In some embodiments, zinc is present in an amount of about 1% to about 30% w/w of the composition. For example, about 1% to about 5%, about 1% to about 10%, about 1% to about 15%, about 1% to about 20%, about 1% to about 25%, about 25% to about 30%, about 20% to about 30%, about 15% to about 30%, about 10% to about 30%, about 5% to about 30%, about 5% to about 29%, or about 15% to about 29% w/w of the composition. In some embodiments, zinc is present in an amount of about 5% to about 15% w/w of the composition. For example, about 5% to about 6%, about 5% to about 7%, about 5% to about 8%, about 5% to about 9%, about 5% to about 10%, about 5% to about 11%, about 5% to about 12%, about 5% to about 13%, about 5% to about 14%, about 14% to about 15%, about 13% to about 15%, about 12% to about 15%, about 11% to about 15%, about 10% to about 15%, about 8% to about 15%, about 7% to about 15%, about 6% to about 15% w/w of the composition. In some embodiments, zinc is present in an amount of about 5%, about 5.5%, about 6%, about 6.5%, about 7%, about 7.5%, about 8%, about 8.5%, about 9%, about 9.1%, about 9.5%, about 10%, about 10.5%, about 11%, about 11.5%, about 12%, about 12.5%, about 13%, about 13.5%, about 14%, about 14.5%, or about 15% w/w of the composition.

In some embodiments, a composition as described herein includes a carboxylic acid that can modulate testosterone synthesis. In some embodiments, a composition as described herein includes a carboxylic acid that decreases testosterone degradation. In some embodiments, a composition as described herein includes a carboxylic acid that decreases oxidative stress.

In some embodiments, a carboxylic acid is present in an amount of about 1% to about 30% w/w of the composition. For example, about 1% to about 5%, about 1% to about 10%, about 1% to about 15%, about 1% to about 20%, about 1% to about 25%, about 25% to about 30%, about 20% to about 30%, about 15% to about 30%, about 10% to about 30%, about 5% to about 30%, about 5% to about 29%, or about 15% to about 29% w/w of the composition. In some embodiments, the carboxylic acid is present in an amount of about 2% to about 10% w/w of the composition. For example, about 2% to about 3%, about 2% to about 4%, about 2% to about 5%, about 2% to about 6%, about 2% to about 7%, about 2% to about 8%, about 2% to about 9%, about 9% to about 10%, about 8% to about 10%, about 7% to about 10%, about 6% to about 10%, about 5% to about 10%, about 4% to about 10%, or about 3% to about 10% w/w of the composition. In some embodiments, the carboxylic acid is present in an amount of about 2%, about 2.1%, about 2.3%, about 2.5%, about 2.7%, about 3%, about 3.1%, about 3.3%, about 3.5%, about 3.7%, about 4%, about 4.1%, about 4.3%, about 4.5%, about 4.7%, about 5%, about 5.1%, about 5.3%, about 5.5%, about 5.7%, about 5.9%, about 6%, about 6.1%, about 6.3%, about 6.5%, about 6.7%, about 6.9%, about 7%, about 7.1%, about 7.3%, about 7.5%, about 7.7%, about 7.9%, about 8%, about 8.1%, about 8.3%, about 8.5%, about 8.7%, about 8.9%, about 9%, about 9.1%, about 9.3%, about 9.5%, about 9.7%, about 9.9%, or about 10% w/w of the composition.

In some embodiments, the carboxylic acid is a cinnamate. In some embodiments, the cinnamate is selected from the group consisting of: picroside II, clocinnamox, hydrocinnamic acid, rosmarinic acid, and caffeic acid, and a combination thereof.

In some embodiments, the carboxylic acid is caffeic acid. In some embodiments, caffeic acid is present in an amount of about 1% to about 30% w/w of the composition. For example, about 1% to about 5%, about 1% to about 10%, about 1% to about 15%, about 1% to about 20%, about 1% to about 25%, about 25% to about 30%, about 20% to about 30%, about 15% to about 30%, about 10% to about 30%, about 5% to about 30%, about 5% to about 29%, or about 15% to about 29% w/w of the composition. In some embodiments, caffeic acid is present in an amount of about 2% to about 10% w/w of the composition. For example, about 2% to about 3%, about 2% to about 4%, about 2% to about 5%, about 2% to about 6%, about 2% to about 7%, about 2% to about 8%, about 2% to about 9%, about 9% to about 10%, about 8% to about 10%, about 7% to about 10%, about 6% to about 10%, about 5% to about 10%, about 4% to about 10%, or about 3% to about 10% w/w of the composition. In some embodiments, caffeic acid is present in an amount of about 2%, about 2.1%, about 2.3%, about 2.5%, about 2.7%, about 3%, about 3.1%, about 3.3%, about 3.5%, about 3.7%, about 4%, about 4.1%, about 4.3%, about 4.5%, about 4.7%, about 5%, about 5.1%, about 5.3%, about 5.5%, about 5.7%, about 5.9%, about 6%, about 6.1%, about 6.3%, about 6.5%, about 6.7%, about 6.9%, about 7%, about 7.1%, about 7.3%, about 7.5%, about 7.7%, about 7.9%, about 8%, about 8.1%, about 8.3%, about 8.5%, about 8.7%, about 8.9%, about 9%, about 9.1%, about 9.3%, about 9.5%, about 9.7%, about 9.9%, or about 10% w/w of the composition.

In some embodiments, a composition as described herein includes a carboxylic acid that can modulate testosterone synthesis. In some embodiments, a composition as described herein includes a carboxylic acid that decreases testosterone degradation. In some embodiments, a composition as described herein includes a carboxylic acid that decreases oxidative stress.

In some embodiments, a carboxylic acid is present in an amount of about 0.5% to about 20% w/w of the composition. For example, about 0.5% to about 1%, about 0.5% to about 5%, about 0.5% to about 10%, about 0.5% to about 15%, about 0.5% to about 20%, about 15% to about 20%, about 10% to about 20%, about 5% to about 20%, or about 1% to about 20% w/w of the composition. In some embodiments, the carboxylic acid is present in an amount of about 2% to about 10% w/w of the composition. For example, about 2% to about 3%, about 2% to about 4%, about 2% to about 5%, about 2% to about 6%, about 2% to about 7%, about 2% to about 8%, about 2% to about 9%, about 9% to about 10%, about 8% to about 10%, about 7% to about 10%, about 6% to about 10%, about 5% to about 10%, about 4% to about 10%, or about 3% to about 10% w/w of the composition. In some embodiments, the carboxylic acid is present in an amount of about 2%, about 2.2%, about 2.4%, about 2.6%, about 2.8%, about 3%, about 3.2%, about 3.4%, about 3.6%, about 3.8%, about 4%, about 4.2%, about 4.4%, about 4.6%, about 4.8%, about 5%, about 5.2%, about 5.4%, about 5.6%, about 5.8%, about 6%, about 6.2%, about 6.4%, about 6.6%, about 6.8%, about 7%, about 7.2%, about 7.4%, about 7.6%, about 7.8%, about 8%, about 8.2%, about 8.4%, about 8.6%, about 8.8%, about 9%, about 9.2%, about 9.4%, about 9.6%, about 9.8%, or about 10% w/w of the composition.

In some embodiments, the carboxylic acid is a ketoaldonic acid. In some embodiments, the ketoaldonic acid is selected from the group consisting of: D- or L-ascorbic acid (vitamin C), erythorbic acid, gulonic acid, and a combination thereof.

In some embodiments, the carboxylic acid is ascorbic acid (vitamin C). In some embodiments, vitamin C is present in an amount of about 0.5% to about 20% w/w of the composition. For example, about 0.5% to about 1%, about 0.5% to about 5%, about 0.5% to about 10%, about 0.5% to about 15%, about 0.5% to about 20%, about 15% to about 20%, about 10% to about 20%, about 5% to about 20%, or about 1% to about 20% w/w of the composition. In some embodiments, vitamin C is present in an amount of about 2% to about 10% w/w of the composition. For example, about 2% to about 3%, about 2% to about 4%, about 2% to about 5%, about 2% to about 6%, about 2% to about 7%, about 2% to about 8%, about 2% to about 9%, about 9% to about 10%, about 8% to about 10%, about 7% to about 10%, about 6% to about 10%, about 5% to about 10%, about 4% to about 10%, or about 3% to about 10% w/w of the composition. In some embodiments, vitamin C is present in an amount of about 2%, about 2.2%, about 2.4%, about 2.6%, about 2.8%, about 3%, about 3.2%, about 3.4%, about 3.6%, about 3.8%, about 4%, about 4.2%, about 4.4%, about 4.6%, about 4.8%, about 5%, about 5.2%, about 5.4%, about 5.6%, about 5.8%, about 6%, about 6.2%, about 6.4%, about 6.6%, about 6.8%, about 7%, about 7.2%, about 7.4%, about 7.6%, about 7.8%, about 8%, about 8.2%, about 8.4%, about 8.6%, about 8.8%, about 9%, about 9.2%, about 9.4%, about 9.6%, about 9.8%, or about 10% w/w of the composition.

In some embodiments, a composition as described herein includes a flavone that can modulate testosterone synthesis. In some embodiments, a composition as described herein includes a flavone that decreases testosterone degradation. In some embodiments, a composition as described herein includes a flavone that decreases oxidative stress.

In some embodiments, a flavone is present in an amount of about 0.5% to about 25% w/w of the composition. For example, about 0.5% to about 1%, about 0.5% to about 5%, about 0.5% to about 10%, about 0.5% to about 15%, about 0.5% to about 20%, about 0.5% to about 25%, about 20% to about 25%, about 15% to about 25%, about 10% to about 25%, about 5% to about 25%, or about 1% to about 25% w/w of the composition. In some embodiments, the flavone is present in an amount of about 2% to about 10% w/w of the composition. For example, about 2% to about 3%, about 2% to about 4%, about 2% to about 5%, about 2% to about 6%, about 2% to about 7%, about 2% to about 8%, about 2% to about 9%, about 9% to about 10%, about 8% to about 10%, about 7% to about 10%, about 6% to about 10%, about 5% to about 10%, about 4% to about 10%, or about 3% to about 10% w/w of the composition. In some embodiments, the flavone is present in an amount of about 2%, about 2.1%, about 2.3%, about 2.5%, about 2.7%, about 3%, about 3.1%, about 3.3%, about 3.5%, about 3.7%, about 4%, about 4.1%, about 4.3%, about 4.5%, about 4.7%, about 5%, about 5.1%, about 5.3%, about 5.5%, about 5.7%, about 5.9%, about 6%, about 6.1%, about 6.3%, about 6.5%, about 6.7%, about 6.9%, about 7%, about 7.1%, about 7.3%, about 7.5%, about 7.7%, about 7.9%, about 8%, about 8.1%, about 8.3%, about 8.5%, about 8.7%, about 8.9%, about 9%, about 9.1%, about 9.3%, about 9.5%, about 9.7%, about 9.9%, or about 10% w/w of the composition. In some embodiments, the flavone is present in an amount of about 1% to about 10% w/w of the composition. In some embodiments, the flavone is present in an amount of about 1.5% to about 5% w/w of the composition. In some embodiments, the flavone is present in an amount of about 2.9% w/w of the composition.

In some embodiments, the flavone is a pentahydroxyflavone. In some embodiments, the pentahydroxyflavone is selected from the group consisting of: quercetin, luteolin, and a combination thereof.

In some embodiments, the flavone is quercetin. In some embodiments, quercetin is present in an amount of about 0.5% to about 30% w/w of the composition. In some embodiments, quercetin is present in an amount of about 0.5% to about 25% w/w of the composition. For example, about 0.5% to about 1%, about 0.5% to about 5%, about 0.5% to about 10%, about 0.5% to about 15%, about 0.5% to about 20%, about 0.5% to about 30%, about 20% to about 30%, about 15% to about 30%, about 10% to about 30%, about 5% to about 30%, or about 1% to about 30% w/w of the composition. In some embodiments, quercetin is present in an amount of about 2% to about 15% w/w of the composition. In some embodiments, quercetin is present in an amount of about 2% to about 10% w/w of the composition. For example, about 2% to about 3%, about 2% to about 4%, about 2% to about 5%, about 2% to about 6%, about 2% to about 7%, about 2% to about 8%, about 2% to about 9%, about 9% to about 10%, about 8% to about 15%, about 9% to about 15%, about 10% to about 15%, about 11% to about 15%, about 12% to about 15%, about 13% to about 15%, about 14% to about 15%, about 7% to about 10%, about 6% to about 10%, about 5% to about 10%, about 4% to about 10%, or about 3% to about 10% w/w of the composition. In some embodiments, quercetin is present in an amount of about 2%, about 2.1%, about 2.3%, about 2.5%, about 2.7%, about 3%, about 3.1%, about 3.3%, about 3.5%, about 3.7%, about 4%, about 4.1%, about 4.3%, about 4.5%, about 4.7%, about 5%, about 5.1%, about 5.3%, about 5.5%, about 5.7%, about 5.9%, about 6%, about 6.1%, about 6.3%, about 6.5%, about 6.7%, about 6.9%, about 7%, about 7.1%, about 7.3%, about 7.5%, about 7.7%, about 7.9%, about 8%, about 8.1%, about 8.3%, about 8.5%, about 8.7%, about 8.9%, about 9%, about 9.1%, about 9.3%, about 9.5%, about 9.7%, about 9.9%, or about 10% w/w of the composition.

In some embodiments, a flavone is present in an amount of about 0.5% to about 25% w/w of the composition. For example, about 0.5% to about 1%, about 0.5% to about 5%, about 0.5% to about 10%, about 0.5% to about 15%, about 0.5% to about 20%, about 0.5% to about 25%, about 20% to about 25%, about 15% to about 25%, about 10% to about 25%, about 5% to about 25%, or about 1% to about 25% w/w of the composition. In some embodiments, the flavone is present in an amount of about 2% to about 10% w/w of the composition. For example, about 2% to about 3%, about 2% to about 4%, about 2% to about 5%, about 2% to about 6%, about 2% to about 7%, about 2% to about 8%, about 2% to about 9%, about 9% to about 10%, about 8% to about 10%, about 7% to about 10%, about 6% to about 10%, about 5% to about 10%, about 4% to about 10%, or about 3% to about 10% w/w of the composition. In some embodiments, the flavone is present in an amount of about 2%, about 2.1%, about 2.3%, about 2.5%, about 2.7%, about 3%, about 3.1%, about 3.3%, about 3.5%, about 3.7%, about 4%, about 4.1%, about 4.3%, about 4.5%, about 4.7%, about 5%, about 5.1%, about 5.3%, about 5.5%, about 5.7%, about 5.9%, about 6%, about 6.1%, about 6.3%, about 6.5%, about 6.7%, about 6.9%, about 7%, about 7.1%, about 7.3%, about 7.5%, about 7.7%, about 7.9%, about 8%, about 8.1%, about 8.3%, about 8.5%, about 8.7%, about 8.9%, about 9%, about 9.1%, about 9.3%, about 9.5%, about 9.7%, about 9.9%, or about 10% w/w of the composition.

In some embodiments, the flavone is a tetrahydroxyflavone. In some embodiments, the tetrahydroxyflavone is selected from the group consisting of: nigrasin I, rutin, macaranone B, avicularin, and a combination thereof.

In some embodiments, the flavone is rutin. In some embodiments, rutin is present in an amount of about 0.5% to about 25% w/w of the composition. For example, about 0.5% to about 1%, about 0.5% to about 5%, about 0.5% to about 10%, about 0.5% to about 15%, about 0.5% to about 20%, about 0.5% to about 25%, about 20% to about 25%, about 15% to about 25%, about 10% to about 25%, about 5% to about 25%, or about 1% to about 25% w/w of the composition. In some embodiments, rutin is present in an amount of about 2% to about 10% w/w of the composition. For example, about 2% to about 3%, about 2% to about 4%, about 2% to about 5%, about 2% to about 6%, about 2% to about 7%, about 2% to about 8%, about 2% to about 9%, about 9% to about 10%, about 8% to about 10%, about 7% to about 10%, about 6% to about 10%, about 5% to about 10%, about 4% to about 10%, or about 3% to about 10% w/w of the composition. In some embodiments, rutin is present in an amount of about 2%, about 2.1%, about 2.3%, about 2.5%, about 2.7%, about 3%, about 3.1%, about 3.3%, about 3.5%, about 3.7%, about 4%, about 4.1%, about 4.3%, about 4.5%, about 4.7%, about 5%, about 5.1%, about 5.3%, about 5.5%, about 5.7%, about 5.9%, about 6%, about 6.1%, about 6.3%, about 6.5%, about 6.7%, about 6.9%, about 7%, about 7.1%, about 7.3%, about 7.5%, about 7.7%, about 7.9%, about 8%, about 8.1%, about 8.3%, about 8.5%, about 8.7%, about 8.9%, about 9%, about 9.1%, about 9.3%, about 9.5%, about 9.7%, about 9.9%, or about 10% w/w of the composition.

In some embodiments, a flavone is present in an amount of about 0.01% to about 5% w/w of the composition. For example, about 0.01% to about 1%, about 0.01% to about 2%, about 0.01% to about 3%, about 0.01% to about 3%, about 0.01% to about 4%, about 4% to about 5%, about 3% to about 5%, about 2% to about 5%, or about 1% to about 5% w/w of the composition. In some embodiments, the flavone is present in an amount of about 0.01% to about 1.5% w/w of the composition. For example, about 0.01% to about 0.1%, about 0.01% to about 0.2%, about 0.01% to about 0.3%, about 0.01% to about 0.4%, about 0.01% to about 0.5%, about 0.01% to about 0.6%, about 0.01% to about 0.7%, about 0.01% to about 0.8%, about 0.01% to about 0.9%, about 0.01% to about 1%, about 0.01% to about 1.1%, about 0.01% to about 1.2%, about 0.01% to about 1.3%, about 0.01% to about 1.4%, about 1.4% to about 1.5%, about 1.3% to about 1.5%, about 1.2% to about 1.5%, about 1.1% to about 1.5%, about 1% to about 1.5%, about 0.9% to about 1.5%, about 0.8% to about 1.5%, about 0.7% to about 1.5%, about 0.6% to about 1.5%, about 0.5% to about 1.5%, about 0.4% to about 1.5%, about 0.3% to about 1.5%, about 0.2% to about 1.5%, or about 0.1% to about 1.5% w/w of the composition. In some embodiments, the flavone is present in an amount of about 0.01%, about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1%, about 1.05%, about 1.1%, about 1.15%, about 1.2%, about 1.25%, about 1.3%, about 1.35%, about 1.4%, about 1.45%, or about 1.5% w/w of the composition. In some embodiments, a flavone is present in an amount of about 0.5% to about 2% w/w of the composition. In some embodiments, a flavone is present in an amount of about 0.1% to about 1% w/w of the composition. In some embodiments, a flavone is present in an amount of about 0.7% w/w of the composition. In some embodiments, a flavone is present in an amount of about 0.7% w/w of the composition.

In some embodiments, the flavone is a trihydroxyflavone. In some embodiments, the trihydroxyflavone is selected from the group consisting of: apigenin, baicalein, norwogonin, galangin, and a combination thereof.

In some embodiments, the flavone is apigenin. In some embodiments, apigenin is present in an amount of about 0.01% to about 5% w/w of the composition. For example, about 0.01% to about 1%, about 0.01% to about 2%, about 0.01% to about 3%, about 0.01% to about 3%, about 0.01% to about 4%, about 4% to about 5%, about 3% to about 5%, about 2% to about 5%, or about 1% to about 5% w/w of the composition. In some embodiments, apigenin is present in an amount of about 0.01% to about 1.5% w/w of the composition. For example, about 0.01% to about 0.1%, about 0.01% to about 0.2%, about 0.01% to about 0.3%, about 0.01% to about 0.4%, about 0.01% to about 0.5%, about 0.01% to about 0.6%, about 0.01% to about 0.7%, about 0.01% to about 0.8%, about 0.01% to about 0.9%, about 0.01% to about 1%, about 0.01% to about 1.1%, about 0.01% to about 1.2%, about 0.01% to about 1.3%, about 0.01% to about 1.4%, about 1.4% to about 1.5%, about 1.3% to about 1.5%, about 1.2% to about 1.5%, about 1.1% to about 1.5%, about 1% to about 1.5%, about 0.9% to about 1.5%, about 0.8% to about 1.5%, about 0.7% to about 1.5%, about 0.6% to about 1.5%, about 0.5% to about 1.5%, about 0.4% to about 1.5%, about 0.3% to about 1.5%, about 0.2% to about 1.5%, or about 0.1% to about 1.5% w/w of the composition. In some embodiments, apigenin is present in an amount of about 0.01%, about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1%, about 1.05%, about 1.1%, about 1.15%, about 1.2%, about 1.25%, about 1.3%, about 1.35%, about 1.4%, about 1.45%, or about 1.5% w/w of the composition.

In some embodiments, a flavone is present in an amount of about 0.05% to about 15% w/w of the composition. For example, about 0.05% to about 1%, about 0.05% to about 3%, about 0.05% to about 6%, about 0.05% to about 9%, about 0.05% to about 12%, about 0.05% to about 12%, about 12% to about 15%, about 9% to about 15%, about 6% to about 15%, about 3% to about 15%, or about 1% to about 15% w/w of the composition. In some embodiments, the flavone is present in an amount of about 0.5% to about 5% w/w of the composition. For example, about 0.5% to about 0.7%, about 0.5% to about 0.9%, about 0.5% to about 1.1%, about 0.5% to about 1.3%, about 0.5% to about 1.5%, about 0.5% to about 1.7%, about 0.5% to about 1.9%, about 0.5% to about 2.1%, about 0.5% to about 2.3%, about 0.5% to about 2.5%, about 0.5% to about 2.7%, about 0.5% to about 2.9%, about 0.5% to about 3.1%, about 0.5% to about 3.3%, about 0.5% to about 3.5%, about 0.5% to about 3.7%, about 0.5% to about 3.9%, about 0.5% to about 4.1%, about 0.5% to about 4.3%, about 0.5% to about 4.5%, about 0.5% to about 4.7%, about 0.5% to about 4.9%, about 4.9% to about 5%, about 4.7% to about 5%, about 4.5% to about 5%, about 4.3% to about 5%, about 4.1% to about 5%, about 3.9% to about 5%, about 3.7% to about 5%, about 3.5% to about 5%, about 3.3% to about 5%, about 3.1% to about 5%, about 2.9% to about 5%, about 2.7% to about 5%, about 2.5% to about 5%, about 2.3% to about 5%, about 2.1% to about 5%, about 1.9% to about 5%, about 1.7% to about 5%, about 1.5% to about 5%, about 1.3% to about 5%, about 1.1% to about 5%, about 0.9% to about 5%, or about 0.7% to about 5% w/w of the composition. In some embodiments, the flavone is present in an amount of about 0.5%, about 0.7%, about 0.9%, about 1%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, or about 5% w/w of the composition. In some embodiments, a flavone is present in an amount of about 0.1% to about 10% w/w of the composition.

In some embodiments, the flavone is a flavanol. In some embodiments, the flavanol is selected from the group consisting of: myrcetin, icariin, sexangularetin, kaempferol, isorhamnetin, and a combination thereof.

In some embodiments, the flavone is icariin. In some embodiments, icariin is present in an amount of about 0.05% to about 15% w/w of the composition. For example, about 0.05% to about 1%, about 0.05% to about 3%, about 0.05% to about 6%, about 0.05% to about 9%, about 0.05% to about 12%, about 0.05% to about 12%, about 12% to about 15%, about 9% to about 15%, about 6% to about 15%, about 3% to about 15%, or about 1% to about 15% w/w of the composition. In some embodiments, icariin is present in an amount of about 0.5% to about 5% w/w of the composition. For example, about 0.5% to about 0.7%, about 0.5% to about 0.9%, about 0.5% to about 1.1%, about 0.5% to about 1.3%, about 0.5% to about 1.5%, about 0.5% to about 1.7%, about 0.5% to about 1.9%, about 0.5% to about 2.1%, about 0.5% to about 2.3%, about 0.5% to about 2.5%, about 0.5% to about 2.7%, about 0.5% to about 2.9%, about 0.5% to about 3.1%, about 0.5% to about 3.3%, about 0.5% to about 3.5%, about 0.5% to about 3.7%, about 0.5% to about 3.9%, about 0.5% to about 4.1%, about 0.5% to about 4.3%, about 0.5% to about 4.5%, about 0.5% to about 4.7%, about 0.5% to about 4.9%, about 4.9% to about 5%, about 4.7% to about 5%, about 4.5% to about 5%, about 4.3% to about 5%, about 4.1% to about 5%, about 3.9% to about 5%, about 3.7% to about 5%, about 3.5% to about 5%, about 3.3% to about 5%, about 3.1% to about 5%, about 2.9% to about 5%, about 2.7% to about 5%, about 2.5% to about 5%, about 2.3% to about 5%, about 2.1% to about 5%, about 1.9% to about 5%, about 1.7% to about 5%, about 1.5% to about 5%, about 1.3% to about 5%, about 1.1% to about 5%, about 0.9% to about 5%, or about 0.7% to about 5% w/w of the composition. In some embodiments, icariin is present in an amount of about 0.5%, about 0.7%, about 0.9%, about 1%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, or about 5% w/w of the composition.

In some embodiments, a flavone is present in an amount of about 0.025% to about 2% w/w of the composition. For example, about 0.025% to about 0.2%, about 0.025% to about 0.4%, about 0.025% to about 0.6%, about 0.025% to about 0.8%, about 0.025% to about 1%, about 0.025% to about 1.2%, about 0.025% to about 1.4%, about 0.025% to about 1.6%, about 0.025% to about 1.8%, about 0.025% to about 1.9%, about 1.9% to about 2%, about 1.8% to about 2%, about 1.6% to about 2%, about 1.4% to about 2%, about 1.2% to about 2%, about 1% to about 2%, about 0.8% to about 2%, about 0.6% to about 2%, about 0.4% to about 2%, about 0.2% to about 2%, about 0.1% to about 2%, or about 0.05% to about 1% w/w of the composition. In some embodiments, the flavone is present in an amount of about 0.025% to about 1% w/w of the composition. For example, about 0.025% to about 0.075, about 0.025% to about 0.125%, about 0.025% to about 0.175%, about 0.025% to about 0.225%, about 0.025% to about 0.275%, about 0.025% to about 0.325%, about 0.025% to about 0.375%, about 0.025% to about 0.425%, about 0.025% to about 0.475%, about 0.025% to about 0.525%, about 0.025% to about 0.575%, about 0.025% to about 0.625%, about 0.025% to about 0.675%, about 0.025% to about 0.725%, about 0.025% to about 0.775%, about 0.025% to about 0.825%, about 0.025% to about 0.875%, about 0.025% to about 0.925%, about 0.025% to about 0.975%, about 0.975% to about 1%, about 0.925% to about 1%, about 0.875% to about 1%, about 0.825% to about 1%, about 0.775% to about 1%, about 0.725% to about 1%, about 0.675% to about 1%, about 0.625% to about 1%, about 0.575% to about 1%, about 0.525% to about 1%, about 0.475% to about 1%, about 0.425% to about 1%, about 0.375% to about 1%, about 0.325% to about 1%, about 0.275% to about 1%, about 0.225% to about 1%, about 0.175% to about 1%, about 0.125% to about 1%, about 0.075% to about 1%, or about 0.05% to about 1% w/w of the composition. In some embodiments, the flavone is present in an amount of about 0.025%, about 0.05%, about 0.075%, about 0.1%, about 0.125%, about 0.15%, about 0.175%, about 0.2%, about 0.225%, about 0.25%, about 0.275%, about 0.3, about 0.325%, about 0.35%, about 0.375%, about 0.4%, about 0.425%, about 0.45%, about 0.475%, about 0.5%, about 0.525%, about 0.55%, about 0.575%, about 0.6%, about 0.625%, about 0.65%, about 0.65%, about 0.675%, about 0.7%, about 0.725%, about 0.75%, about 0.775%, about 0.8%, about 0.825%, about 0.85%, about 0.875%, about 0.9%, about 0.925%, about 0.95%, about 0.975%, or about 1% w/w of the composition.

In some embodiments, the flavone is a flavanol. In some embodiments, the flavanol is selected from the group consisting of: myrcetin, icariin, sexangularetin, kaempferol, isorhamnetin, and a combination thereof.

In some embodiments, the flavone is kaempferol. In some embodiments kaempferol is present in an amount of about 0.025% to about 2% w/w of the composition. For example, about 0.025% to about 0.2%, about 0.025% to about 0.4%, about 0.025% to about 0.6%, about 0.025% to about 0.8%, about 0.025% to about 1%, about 0.025% to about 1.2%, about 0.025% to about 1.4%, about 0.025% to about 1.6%, about 0.025% to about 1.8%, about 0.025% to about 1.9%, about 1.9% to about 2%, about 1.8% to about 2%, about 1.6% to about 2%, about 1.4% to about 2%, about 1.2% to about 2%, about 1% to about 2%, about 0.8% to about 2%, about 0.6% to about 2%, about 0.4% to about 2%, about 0.2% to about 2%, about 0.1% to about 2%, or about 0.05% to about 1% w/w of the composition. In some embodiments, kaempferol is present in an amount of about 0.025% to about 1% w/w of the composition. For example, about 0.025% to about 0.075, about 0.025% to about 0.125%, about 0.025% to about 0.175%, about 0.025% to about 0.225%, about 0.025% to about 0.275%, about 0.025% to about 0.325%, about 0.025% to about 0.375%, about 0.025% to about 0.425%, about 0.025% to about 0.475%, about 0.025% to about 0.525%, about 0.025% to about 0.575%, about 0.025% to about 0.625%, about 0.025% to about 0.675%, about 0.025% to about 0.725%, about 0.025% to about 0.775%, about 0.025% to about 0.825%, about 0.025% to about 0.875%, about 0.025% to about 0.925%, about 0.025% to about 0.975%, about 0.975% to about 1%, about 0.925% to about 1%, about 0.875% to about 1%, about 0.825% to about 1%, about 0.775% to about 1%, about 0.725% to about 1%, about 0.675% to about 1%, about 0.625% to about 1%, about 0.575% to about 1%, about 0.525% to about 1%, about 0.475% to about 1%, about 0.425% to about 1%, about 0.375% to about 1%, about 0.325% to about 1%, about 0.275% to about 1%, about 0.225% to about 1%, about 0.175% to about 1%, about 0.125% to about 1%, about 0.075% to about 1%, or about 0.05% to about 1% w/w of the composition. In some embodiments, kaempferol is present in an amount of about 0.025%, about 0.05%, about 0.075%, about 0.1%, about 0.125%, about 0.15%, about 0.175%, about 0.2%, about 0.225%, about 0.25%, about 0.275%, about 0.3, about 0.325%, about 0.35%, about 0.375%, about 0.4%, about 0.425%, about 0.45%, about 0.475%, about 0.5%, about 0.525%, about 0.55%, about 0.575%, about 0.6%, about 0.625%, about 0.65%, about 0.65%, about 0.675%, about 0.7%, about 0.725%, about 0.75%, about 0.775%, about 0.8%, about 0.825%, about 0.85%, about 0.875%, about 0.9%, about 0.925%, about 0.95%, about 0.975%, or about 1% w/w of the composition.

In some embodiments, a composition as described herein includes a flavan that can modulate testosterone synthesis. In some embodiments, a composition as described herein includes a flavan that decreases testosterone degradation. In some embodiments, a composition as described herein includes a flavan that decreases oxidative stress.

In some embodiments, a flavan is present in an amount of about 0.025% to about 2% w/w of the composition. For example, about 0.025% to about 0.2%, about 0.025% to about 0.4%, about 0.025% to about 0.6%, about 0.025% to about 0.8%, about 0.025% to about 1%, about 0.025% to about 1.2%, about 0.025% to about 1.4%, about 0.025% to about 1.6%, about 0.025% to about 1.8%, about 0.025% to about 1.9%, about 1.9% to about 2%, about 1.8% to about 2%, about 1.6% to about 2%, about 1.4% to about 2%, about 1.2% to about 2%, about 1% to about 2%, about 0.8% to about 2%, about 0.6% to about 2%, about 0.4% to about 2%, about 0.2% to about 2%, about 0.1% to about 2%, or about 0.05% to about 1% w/w of the composition. In some embodiments, the flavan is present in an amount of about 0.025% to about 1% w/w of the composition. For example, about 0.025% to about 0.075, about 0.025% to about 0.125%, about 0.025% to about 0.175%, about 0.025% to about 0.225%, about 0.025% to about 0.275%, about 0.025% to about 0.325%, about 0.025% to about 0.375%, about 0.025% to about 0.425%, about 0.025% to about 0.475%, about 0.025% to about 0.525%, about 0.025% to about 0.575%, about 0.025% to about 0.625%, about 0.025% to about 0.675%, about 0.025% to about 0.725%, about 0.025% to about 0.775%, about 0.025% to about 0.825%, about 0.025% to about 0.875%, about 0.025% to about 0.925%, about 0.025% to about 0.975%, about 0.975% to about 1%, about 0.925% to about 1%, about 0.875% to about 1%, about 0.825% to about 1%, about 0.775% to about 1%, about 0.725% to about 1%, about 0.675% to about 1%, about 0.625% to about 1%, about 0.575% to about 1%, about 0.525% to about 1%, about 0.475% to about 1%, about 0.425% to about 1%, about 0.375% to about 1%, about 0.325% to about 1%, about 0.275% to about 1%, about 0.225% to about 1%, about 0.175% to about 1%, about 0.125% to about 1%, about 0.075% to about 1%, or about 0.05% to about 1% w/w of the composition. In some embodiments, the flavan is present in an amount of about 0.025%, about 0.05%, about 0.075%, about 0.1%, about 0.125%, about 0.15%, about 0.175%, about 0.2%, about 0.225%, about 0.25%, about 0.275%, about 0.3, about 0.325%, about 0.35%, about 0.375%, about 0.4%, about 0.425%, about 0.45%, about 0.475%, about 0.5%, about 0.525%, about 0.55%, about 0.575%, about 0.6%, about 0.625%, about 0.65%, about 0.65%, about 0.675%, about 0.7%, about 0.725%, about 0.75%, about 0.775%, about 0.8%, about 0.825%, about 0.85%, about 0.875%, about 0.9%, about 0.925%, about 0.95%, about 0.975%, or about 1% w/w of the composition.

In some embodiments, the flavan is a flavan 3-ols. In some embodiments, the flavan 3-ol is selected from the group consisting of: epicatechin, catechin, epigallocatechin, fisetinidol, EGCG, and a combination thereof.

In some embodiments, the flavan is epicatechin. In some embodiments, epicatechin is present in an amount of about 0.025% to about 2% w/w of the composition. For example, about 0.025% to about 0.2%, about 0.025% to about 0.4%, about 0.025% to about 0.6%, about 0.025% to about 0.8%, about 0.025% to about 1%, about 0.025% to about 1.2%, about 0.025% to about 1.4%, about 0.025% to about 1.6%, about 0.025% to about 1.8%, about 0.025% to about 1.9%, about 1.9% to about 2%, about 1.8% to about 2%, about 1.6% to about 2%, about 1.4% to about 2%, about 1.2% to about 2%, about 1% to about 2%, about 0.8% to about 2%, about 0.6% to about 2%, about 0.4% to about 2%, about 0.2% to about 2%, about 0.1% to about 2%, or about 0.05% to about 1% w/w of the composition. In some embodiments, epicatechin is present in an amount of about 0.025% to about 1% w/w of the composition. For example, about 0.025% to about 0.075, about 0.025% to about 0.125%, about 0.025% to about 0.175%, about 0.025% to about 0.225%, about 0.025% to about 0.275%, about 0.025% to about 0.325%, about 0.025% to about 0.375%, about 0.025% to about 0.425%, about 0.025% to about 0.475%, about 0.025% to about 0.525%, about 0.025% to about 0.575%, about 0.025% to about 0.625%, about 0.025% to about 0.675%, about 0.025% to about 0.725%, about 0.025% to about 0.775%, about 0.025% to about 0.825%, about 0.025% to about 0.875%, about 0.025% to about 0.925%, about 0.025% to about 0.975%, about 0.975% to about 1%, about 0.925% to about 1%, about 0.875% to about 1%, about 0.825% to about 1%, about 0.775% to about 1%, about 0.725% to about 1%, about 0.675% to about 1%, about 0.625% to about 1%, about 0.575% to about 1%, about 0.525% to about 1%, about 0.475% to about 1%, about 0.425% to about 1%, about 0.375% to about 1%, about 0.325% to about 1%, about 0.275% to about 1%, about 0.225% to about 1%, about 0.175% to about 1%, about 0.125% to about 1%, about 0.075% to about 1%, or about 0.05% to about 1% w/w of the composition. In some embodiments, epicatechin is present in an amount of about 0.025%, about 0.05%, about 0.075%, about 0.1%, about 0.125%, about 0.15%, about 0.175%, about 0.2%, about 0.225%, about 0.25%, about 0.275%, about 0.3, about 0.325%, about 0.35%, about 0.375%, about 0.4%, about 0.425%, about 0.45%, about 0.475%, about 0.5%, about 0.525%, about 0.55%, about 0.575%, about 0.6%, about 0.625%, about 0.65%, about 0.65%, about 0.675%, about 0.7%, about 0.725%, about 0.75%, about 0.775%, about 0.8%, about 0.825%, about 0.85%, about 0.875%, about 0.9%, about 0.925%, about 0.95%, about 0.975%, or about 1% w/w of the composition.

In some embodiments, a flavan is present in an amount of about 0.5% to about 25% w/w of the composition. For example, about 0.5% to about 1%, about 0.5% to about 5%, about 0.5% to about 10%, about 0.5% to about 15%, about 0.5% to about 20%, about 0.5% to about 25%, about 20% to about 25%, about 15% to about 25%, about 10% to about 25%, about 5% to about 25%, or about 1% to about 25% w/w of the composition. In some embodiments, the flavan is present in an amount of about 2% to about 10% w/w of the composition. For example, about 2% to about 3%, about 2% to about 4%, about 2% to about 5%, about 2% to about 6%, about 2% to about 7%, about 2% to about 8%, about 2% to about 9%, about 9% to about 10%, about 8% to about 10%, about 7% to about 10%, about 6% to about 10%, about 5% to about 10%, about 4% to about 10%, or about 3% to about 10% w/w of the composition. In some embodiments, the flavan is present in an amount of about 2%, about 2.1%, about 2.3%, about 2.5%, about 2.7%, about 3%, about 3.1%, about 3.3%, about 3.5%, about 3.7%, about 4%, about 4.1%, about 4.3%, about 4.5%, about 4.7%, about 5%, about 5.1%, about 5.3%, about 5.5%, about 5.7%, about 5.9%, about 6%, about 6.1%, about 6.3%, about 6.5%, about 6.7%, about 6.9%, about 7%, about 7.1%, about 7.3%, about 7.5%, about 7.7%, about 7.9%, about 8%, about 8.1%, about 8.3%, about 8.5%, about 8.7%, about 8.9%, about 9%, about 9.1%, about 9.3%, about 9.5%, about 9.7%, about 9.9%, or about 10% w/w of the composition.

In some embodiments, the flavan is a flavan 3-ol. In some embodiments, the flavan 3-ol is selected from the group consisting of: epicatechin, catechin, epigallocatechin, fisetinidol, EGCG, and a combination thereof.

In some embodiments, the flavan is EGCG. In some embodiments, EGCG is present in an amount of about 0.5% to about 25% w/w of the composition. For example, about 0.5% to about 1%, about 0.5% to about 5%, about 0.5% to about 10%, about 0.5% to about 15%, about 0.5% to about 20%, about 0.5% to about 25%, about 20% to about 25%, about 15% to about 25%, about 10% to about 25%, about 5% to about 25%, or about 1% to about 25% w/w of the composition. In some embodiments, EGCG is present in an amount of about 2% to about 10% w/w of the composition. For example, about 2% to about 3%, about 2% to about 4%, about 2% to about 5%, about 2% to about 6%, about 2% to about 7%, about 2% to about 8%, about 2% to about 9%, about 9% to about 10%, about 8% to about 10%, about 7% to about 10%, about 6% to about 10%, about 5% to about 10%, about 4% to about 10%, or about 3% to about 10% w/w of the composition. In some embodiments, EGCG is present in an amount of about 2%, about 2.1%, about 2.3%, about 2.5%, about 2.7%, about 3%, about 3.1%, about 3.3%, about 3.5%, about 3.7%, about 4%, about 4.1%, about 4.3%, about 4.5%, about 4.7%, about 5%, about 5.1%, about 5.3%, about 5.5%, about 5.7%, about 5.9%, about 6%, about 6.1%, about 6.3%, about 6.5%, about 6.7%, about 6.9%, about 7%, about 7.1%, about 7.3%, about 7.5%, about 7.7%, about 7.9%, about 8%, about 8.1%, about 8.3%, about 8.5%, about 8.7%, about 8.9%, about 9%, about 9.1%, about 9.3%, about 9.5%, about 9.7%, about 9.9%, or about 10% w/w of the composition.

In some embodiments, a composition as described herein includes a terpenoid that can modulate testosterone synthesis. In some embodiments, a composition as described herein includes a terpenoid that decreases testosterone degradation. In some embodiments, a composition as described herein includes a terpenoid that decreases oxidative stress.

In some embodiments, a terpenoid is present in an amount of about 1% to about 70% w/w of the composition. For example, about 1% to about 5%, about 1% to about 10%, about 1% to about 15%, about 1% to about 20%, about 1% to about 25%, about 1% to about 30%, about 1% to about 35%, about 1% to about 40%, about 1% to about 45%, about 1% to about 50%, about 1% to about 55%, about 1% to about 60%, about 1% to about 65%, about 65% to about 70%, 6 about 0% to about 70%, about 55% to about 70%, about 50% to about 70%, about 45% to about 70%, about 40% to about 70%, about 35% to about 70%, about 30% to about 70%, about 25% to about 70%, about 20% to about 70%, about 15% to about 70%, about 10% to about 70%, or about 5% to about 70% w/w of the composition. In some embodiments, the terpenoid is present in an amount of about 15% to about 35% w/w of the composition. For example, about 15% to about 17%, about 15% to about 19%, about 15% to about 21%, about 15% to about 23%, about 15% to about 25%, about 15% to about 27%, about 15% to about 29%, about 15% to about 31%, about 15% to about 33%, about 33% to about 35%, about 31% to about 35%, about 29% to about 35%, about 27% to about 35%, about 25% to about 35%, about 23% to about 35%, about 21% to about 35%, about 19% to about 35%, or about 17% to about 35% w/w of the composition. In some embodiments, the terpenoid is present in an amount of about 2%, about 15%, about 16%, about 17%, about 18%, about 19%, about 19.5%, about 19.6%, about 19.9%, about 20%, about 20.3%, about 20.6%, about 20.7%, about 20.9%, about 21%, about 21.1%, about 21.3%, about 21.5%, about 21.7%, about 21.9%, about 22%, about 23%, about 24%, about 25%, about 26%, about 27%, about 28%, about 29%, about 30%, about 31%, about 32%, about 34%, or about 35% w/w of the composition. In some embodiments, the terpenoid is present in an amount of about 21.7% w/w of the composition.

In some embodiments, the terpenoid is a triterpenoid. In some embodiments, the triterpenoid is selected from the group consisting of: hypodiol, tubeimoside, gamma oryzanol, and a combination thereof.

In some embodiments, the terpenoid is gamma oryzanol. In some embodiments, a gamma oryzanol is present in an amount of about 1% to about 70% w/w of the composition. For example, about 1% to about 5%, about 1% to about 10%, about 1% to about 15%, about 1% to about 20%, about 1% to about 25%, about 1% to about 30%, about 1% to about 35%, about 1% to about 40%, about 1% to about 45%, about 1% to about 50%, about 1% to about 55%, about 1% to about 60%, about 1% to about 65%, about 65% to about 70%, 6 about 0% to about 70%, about 55% to about 70%, about 50% to about 70%, about 45% to about 70%, about 40% to about 70%, about 35% to about 70%, about 30% to about 70%, about 25% to about 70%, about 20% to about 70%, about 15% to about 70%, about 10% to about 70%, or about 5% to about 70% w/w of the composition. In some embodiments, gamma oryzanol is present in an amount of about 15% to about 35% w/w of the composition. For example, about 15% to about 17%, about 15% to about 19%, about 15% to about 21%, about 15% to about 23%, about 15% to about 25%, about 15% to about 27%, about 15% to about 29%, about 15% to about 31%, about 15% to about 33%, about 33% to about 35%, about 31% to about 35%, about 29% to about 35%, about 27% to about 35%, about 25% to about 35%, about 23% to about 35%, about 21% to about 35%, about 19% to about 35%, or about 17% to about 35% w/w of the composition. In some embodiments, gamma oryzanol is present in an amount of about 2%, about 15%, about 16%, about 17%, about 18%, about 19%, about 19.5%, about 19.6%, about 19.9%, about 20%, about 20.3%, about 20.6%, about 20.7%, about 20.9%, about 21%, about 21.1%, about 21.3%, about 21.5%, about 21.7%, about 21.9%, about 22%, about 23%, about 24%, about 25%, about 26%, about 27%, about 28%, about 29%, about 30%, about 31%, about 32%, about 34%, or about 35% w/w of the composition.

In some embodiments, a composition as described herein includes an amino acid that can modulate testosterone synthesis. In some embodiments, a composition as described herein includes an amino that decreases testosterone degradation. In some embodiments, a composition as described herein includes an amino acid that decreases oxidative stress.

In some embodiments, an amino acid is present in an amount of about 1% to about 70% w/w of the composition. For example, about 1% to about 5%, about 1% to about 10%, about 1% to about 15%, about 1% to about 20%, about 1% to about 25%, about 1% to about 30%, about 1% to about 35%, about 1% to about 40%, about 1% to about 45%, about 1% to about 50%, about 1% to about 55%, about 1% to about 60%, about 1% to about 65%, about 65% to about 70%, 6 about 0% to about 70%, about 55% to about 70%, about 50% to about 70%, about 45% to about 70%, about 40% to about 70%, about 35% to about 70%, about 30% to about 70%, about 25% to about 70%, about 20% to about 70%, about 15% to about 70%, about 10% to about 70%, or about 5% to about 70% w/w of the composition. In some embodiments, an amino acid is present in an amount of about 15% to about 35% w/w of the composition. For example, about 15% to about 17%, about 15% to about 19%, about 15% to about 21%, about 15% to about 23%, about 15% to about 25%, about 15% to about 27%, about 15% to about 29%, about 15% to about 31%, about 15% to about 33%, about 33% to about 35%, about 31% to about 35%, about 29% to about 35%, about 27% to about 35%, about 25% to about 35%, about 23% to about 35%, about 21% to about 35%, about 19% to about 35%, or about 17% to about 35% w/w of the composition. In some embodiments, the an amino acid is present in an amount of about 2%, about 15%, about 16%, about 17%, about 18%, about 19%, about 19.5%, about 19.6%, about 19.9%, about 20%, about 20.3%, about 20.6%, about 20.7%, about 20.9%, about 21%, about 21.1%, about 21.3%, about 21.5%, about 21.7%, about 21.9%, about 22%, about 23%, about 24%, about 25%, about 26%, about 27%, about 28%, about 29%, about 30%, about 31%, about 32%, about 34%, or about 35% w/w of the composition.

In some embodiments, an amino acid is an α-amino acid. In some embodiments, the α-amino acid is selected from the group consisting of: D-glutamine, L-glutamine, L-alanine, D-alanine, D-cycloserine, N-methylglycine, L-serine, D-serine, N,N,N-trimethylglycine, 3-amino-1-hydroxypyrrolid-2-one, (R)—(N-[3-(4'-fluorophenyl)-3-{4'-phenylphenoxy) propyl])sarcosine, N-methyl-N-[3-[(4-trilfluoromethyl) phenoxy]-3-phenyl-propyl]glycine, D-aspartic acid, and a combination thereof.

In some embodiments, the amino acid is D-aspartic acid. In some embodiments, a D-aspartic acid is present in an amount of about 1% to about 70% w/w of the composition. For example, about 1% to about 5%, about 1% to about 10%, about 1% to about 15%, about 1% to about 20%, about 1% to about 25%, about 1% to about 30%, about 1% to about 35%, about 1% to about 40%, about 1% to about 45%, about 1% to about 50%, about 1% to about 55%, about 1% to about 60%, about 1% to about 65%, about 65% to about 70%, 6 about 0% to about 70%, about 55% to about 70%, about 50% to about 70%, about 45% to about 70%, about 40% to about 70%, about 35% to about 70%, about 30% to about 70%, about 25% to about 70%, about 20% to about 70%, about 15% to about 70%, about 10% to about 70%, or about 5% to about 70% w/w of the composition. In some embodiments, D-aspartic acid is present in an amount of about 15% to about 35% w/w of the composition. For example, about 15% to about 17%, about 15% to about 19%, about 15% to about 21%, about 15% to about 23%, about 15% to about 25%, about 15% to about 27%, about 15% to about 29%, about 15% to about 31%, about 15% to about 33%, about 33% to about 35%, about 31% to about 35%, about 29% to about 35%, about 27% to about 35%, about 25% to about 35%, about 23% to about 35%, about 21% to about 35%, about 19% to about 35%, or about 17% to about 35% w/w of the composition. In some embodiments, D-aspartic acid is present in an amount of about 2%, about 15%, about 16%, about 17%, about 18%, about 19%, about 19.5%, about 19.6%, about 19.9%, about 20%, about 20.3%, about 20.6%, about 20.7%, about 20.9%, about 21%, about 21.1%, about 21.3%, about 21.5%, about 21.7%, about 21.9%, about 22%, about 23%, about 24%, about 25%, about 26%, about 27%, about 28%, about 29%, about 30%, about 31%, about 32%, about 34%, or about 35% w/w of the composition.

In some embodiments, a composition as described herein includes a benzopyran that can modulate testosterone synthesis. In some embodiments, a composition as described herein includes a benzopyran that decreases testosterone degradation. In some embodiments, a composition as described herein includes a benzopyran that decreases oxidative stress.

In some embodiments, a benzopyran is present in an amount of about 1% to about 30% w/w of the composition. For example, about 1% to about 5%, about 1% to about 10%, about 1% to about 15%, about 1% to about 20%, about 1% to about 25%, about 25% to about 30%, about 20% to about 30%, about 15% to about 30%, about 10% to about 30%, about 5% to about 30%, about 5% to about 29%, or about 15% to about 29% w/w of the composition. In some embodiments, the benzopyran is present in an amount of about 5% to about 15% w/w of the composition. For example, about 5% to about 6%, about 5% to about 7%, about 5% to about 8%, about 5% to about 9%, about 5% to about 10%, about 5% to about 11%, about 5% to about 12%, about 5% to about 13%, about 5% to about 14%, about 14% to about 15%, about 13% to about 15%, about 12% to about 15%, about 11% to about 15%, about 10% to about 15%, about 8% to about 15%, about 7% to about 15%, or about 6% to about 15% w/w of the composition. In some embodiments, the benzopyran is present in an amount of about 5%, about 5.5%, about 6%, about 6.5%, about 7%, about 7.5%, about 8%, about 8.5%, about 9%, about 9.1%, about 9.5%, about 10%, about 10.5%, about 11%, about 11.1%, about 11.2%, about 11.3%, about 11.4%, about 11.5%, about, about 11.6%, about 11.7%, about 11.8%, about 11.9%, about 12%, 12.5%, about 13%, about 13.5%, about 14%, about 14.5%, or about 15% w/w of the composition. In some embodiments, a benzopyran is present in an amount of about 3% to about 20% w/w of the composition.

In some embodiments, the benzopyran is a chromanol. In some embodiments, the chromanol is selected from the group consisting of: α-tocopherol, β-tocopherol, γ-tocopherol, δ-tocopherol, α-tocotrienol, β-tocotrienol, γ-tocotrienol, δ-tocotrienol, vitamin E and a combination thereof.

In some embodiments, the benzopyran is vitamin E. In some embodiments, vitamin E is present in an amount of about 1% to about 30% w/w of the composition. For example, about 1% to about 5%, about 1% to about 10%, about 1% to about 15%, about 1% to about 20%, about 1% to about 25%, about 25% to about 30%, about 20% to about 30%, about 15% to about 30%, about 10% to about 30%, about 5% to about 30%, about 5% to about 29%, or about 15% to about 29% w/w of the composition. In some embodiments, vitamin E is present in an amount of about 5% to about 15% w/w of the composition. For example, about 5% to about 6%, about 5% to about 7%, about 5% to about 8%, about 5% to about 9%, about 5% to about 10%, about 5% to about 11%, about 5% to about 12%, about 5% to about 13%, about 5% to about 14%, about 14% to about 15%, about 13% to about 15%, about 12% to about 15%, about 11% to about 15%, about 10% to about 15%, about 8% to about 15%, about 7% to about 15%, about 6% to about 15% w/w of the composition. In some embodiments, the vitamin E is present in an amount of about 5%, about 5.5%, about 6%, about 6.5%, about 7%, about 7.5%, about 8%, about 8.5%, about 9%, about 9.1%, about 9.5%, about 10%, about 10.5%, about 11%, about 11.1%, about 11.2%, about 11.3%, about 11.4%, about 11.5%, about, about 11.6%, about 11.7%, about 11.8%, about 11.9%, about 12%, 12.5%, about 13%, about 13.5%, about 14%, about 14.5%, or about 15% w/w of the composition.

In some embodiments, a composition as described herein includes a glycoside that can modulate testosterone synthesis. In some embodiments, a composition as described herein includes a glycoside that decreases testosterone degradation. In some embodiments, a composition as described herein includes a glycoside that decreases oxidative stress.

As described herein, a "glycoside" refers to a polycyclic organic compound comprising a sugar molecule bound to another functional group such as a terpene or a steroid via a glycosidic bond. Examples of glycosides, without limitation, saponin, ginsenoside Rg1, and ligustroside.

In some embodiments, a glycoside is present in an amount of about 1% to about 30% w/w of the composition. For example, about 1% to about 5%, about 1% to about 10%, about 1% to about 15%, about 1% to about 20%, about 1% to about 25%, about 25% to about 30%, about 20% to about 30%, about 15% to about 30%, about 10% to about 30%, about 5% to about 30%, about 5% to about 29%, or about 15% to about 29% w/w of the composition. In some embodiments, the glycoside is present in an amount of about 5% to about 15% w/w of the composition. For example, about 5% to about 6%, about 5% to about 7%, about 5% to about 8%, about 5% to about 9%, about 5% to about 10%, about 5% to about 11%, about 5% to about 12%, about 5% to about 13%, about 5% to about 14%, about 14% to about 15%, about 13% to about 15%, about 12% to about 15%, about 11% to about 15%, about 10% to about 15%, about 8% to about 15%, about 7% to about 15%, or about 6% to about 15% w/w of the composition. In some embodiments, the glycoside is present in an amount of about 5%, about 5.5%, about 6%, about 6.5%, about 7%, about 7.1%, about 7.2%, about 7.3%, about 7.4%, about 7.5%, about 7.6%, about 7.7%, about 7.8%, about 7.9%, about 8%, about 8.5%, about 9%, about 9.5%, about 10%, about 10.5%, about 11%, about 11.5%, about 12%, about 12.5%, about 13%, about 13.5%, about 14%, about 14.5%, or about 15% w/w of the composition.

In some embodiments, the glycoside is selected from the group consisting of: saponin, ginsenoside Rg1, ligustroside, and a combination thereof.

In some embodiments, the glycoside is saponin. In some embodiments, saponin is present in an amount of about 1% to about 30% w/w of the composition. For example, about 1% to about 5%, about 1% to about 10%, about 1% to about 15%, about 1% to about 20%, about 1% to about 25%, about 25% to about 30%, about 20% to about 30%, about 15% to about 30%, about 10% to about 30%, about 5% to about 30%, about 5% to about 29%, or about 15% to about 29% w/w of the composition. In some embodiments, saponin is present in an amount of about 5% to about 15% w/w of the composition. For example, about 5% to about 6%, about 5% to about 7%, about 5% to about 8%, about 5% to about 9%, about 5% to about 10%, about 5% to about 11%, about 5% to about 12%, about 5% to about 13%, about 5% to about 14%, about 14% to about 15%, about 13% to about 15%, about 12% to about 15%, about 11% to about 15%, about 10% to about 15%, about 8% to about 15%, about 7% to about 15%, about 6% to about 15% w/w of the composition. In some embodiments, the saponin is present in an amount of about 5%, about 5.5%, about 6%, about 6.5%, about 7%, about 7.1%, about 7.2%, about 7.3%, about 7.4%, about 7.5%, about 7.6%, about 7.7%, about 7.8%, about 7.9%, about 8%, about 8.5%, about 9%, about 9.5%, about 10%, about 10.5%, about 11%, about 11.5%, about 12%, about 12.5%, about 13%, about 13.5%, about 14%, about 14.5%, or about 15% w/w of the composition.

In some of any of the above embodiments, the composition further comprises one or more excipients, diluents, or carriers.

In some embodiments, a composition as described herein is formulated for oral delivery. A composition as described herein can be formulated for oral delivery in a variety of ways. For example, the composition can be in the form of a tablet or powder. As another example, a composition as described herein can be in the form of a liquid, solution, suspension, gummy, tablet, powder, soft gelatin capsules, or hard gelatin capsules. Commercial dietary supplements are generally formulated for oral administration. For oral administration, tablets or capsules can be prepared by conventional means with pharmaceutically acceptable excipients such as binding agents, fillers, lubricants, disintegrants, or wetting agents. The tablets can be coated by methods known in the art. Liquid preparations for oral administration can take the form of, for example, solutions, syrups, or suspension, or they can be presented as a dry product for constitution with saline or other suitable liquid vehicle before use. For example, a composition as described herein can be presented as dry powder and dissolved in a suitable liquid carrier. In some embodiments, a composition as described herein can be diluted in a suitable liquid carrier. In some embodiments, a composition as described herein is diluted in an energy drink. In some embodiments, liquid preparations also can contain pharmaceutically acceptable additives such as suspending agents, emulsifying agents, non-aqueous vehicles, preservatives, buffer salts, flavoring agents, coloring agents, and sweetening agents as appropriate. In some embodiments, a composition as described herein can be presented as a stick pack. Preparations for oral administration can be suitably formulated to give controlled release of the compound.

Tablets and powders can be configured to have a unit dosage equal to the daily desired dosage. For example, if a subject desires 1000 mg of a particular composition, each tablet can be 1000 mg in weight. As another example, if a subject desires 1000 mg of a particular composition each tablet can be 500 mg in weight and the subject can take two tablets. The dosages of a particular composition will depend on many factors including the mode of administration. As an example, a composition as described herein can be formulated in a dose such that an individual receives the weight percentages as shown in Table 1, e.g., in a single tablet, divided among 2 or more tablets, or as a powder.

TABLE 1

| Components | Weight Percentage (%) |
|---|---|
| Zinc | 9.1 |
| Caffeic acid | 4.7 |
| Quercetin | 5.9 |
| Apigenin | 0.7 |
| EGCG | 8.0 |
| Vitamin C | 4.6 |
| Rutin | 2.9 |
| Gamma Oryzanol | 21.7 |
| D-Aspartic acid | 21.7 |
| Vitamin E | 11.6 |
| Icariin | 1.3 |
| Kaempferol | 0.1 |
| Epicatechin | 0.3 |
| Saponin | 7.4 |

In addition, a composition provided herein can contain a pharmaceutically acceptable carrier for in vivo administration to a subject. Such pharmaceutically acceptable carriers include, without limitation, sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include water, alcohol, saline, and buffered solutions. Pharmaceutically acceptable carriers also can include physiologically acceptable aqueous vehicles (e.g., physiological saline) or other known carriers appropriate to specific routes of administration. Preservatives, flavorings, and other additives such as, for example, proteins, anti-microbials, chelating agents, inert gases, and the like also can be present in a composition.

Methods

Also provided herein are methods for increasing free testosterone concentration in a subject in need thereof comprising administering to the subject any of the compositions as described herein. Also provided herein are methods for improving low testosterone (Low T) levels in a subject in need thereof comprising administering to the subject any of the compositions as described herein.

In some embodiments, the Low T is associated with one or more of: male hypogonadism, primary testicular failure, undescended testicles, an injury to testes, infection, cancer chemotherapy, mumps orchitis, Klinefelter syndrome, sarcoidosis, obstructive sleep apnea chronic illnesses such as hyperthyroidism, renal failure and cirrhosis, alcoholism, obesity, stress, diabetes mellitus, aging, Kallmann's syndrome, a pituitary tumor or other type of brain tumor located near the pituitary gland, histiocytosis, tuberculosis, opiate addiction, or malnutrition.

In some embodiments, the composition is administered orally.

EXAMPLES

Example 1. In Silico Simulations of Compositions for Improving Low T Levels

Protocol

The in silico simulations were performed using CytoSolve®, a commercially available tool that enables the computational modeling of biomolecular pathways. CytoSolve® can scale and model highly complex biomolecular phenomena by its ability to integrate and couple the computations of smaller biomolecular pathways (see, e.g., Ayyadurai and Forbes-Dewey Jr. *Cellular and Molecular Bioengineering.* 2011, 4(1):28-45; Nordsletten. *IEEE Trans Biomed Eng.* 2011; 58(12):3508-12; Ayyadurai and Deonikar. *Agricultural Sciences.* 2015; 6:630-662; Ayyadurai. *Commun Med Care Compunetics.* 2011; 1:115-168; Koo et al. *Biophys J.* 2013; 104(10):2295-306; Sweeney et al. *Nat Neurosci.* 2016; 19(6):771-83; and Ayyadurai. (2007) Scalable Computational Architecture for Integrating Biological Pathway Models (Doctoral Dissertation, Massachusetts Institute of Technology); each of which is hereby incorporated by reference in its entirety).

Results

FIG. 1 was derived using CytoSolve® to model mechanisms of testosterone metabolism in leydig cells of the testes that included testosterone synthesis, testosterone degradation, and oxidative stress signaling. Once these pathways were integrated using CytoSolve®, the resulting biomolecular computational model was used to identify the ranges of concentrations of zinc, caffeic acid, vitamin C, quercetin, rutin, apigenin, icariin, kaempferol, epicatechin, EGCG, gamma oryzanol, D-aspartic acid, vitamin E, and saponin, that elicit a synergistic effect on the biomarker, free testosterone concentration (see Table 1). Three scenarios were simulated biomolecular computational model on the CytoSolve® platform over a period of about two days: 1) Control (Low T); 2) Effect of composition herein in Table 1 on free testosterone; and, 3) Healthy testosterone concentration. The amounts of zinc, caffeic acid, vitamin C, quercetin, rutin, apigenin, icariin, kaempferol, epicatechin, EGCG, gamma oryzanol, D-aspartic acid, vitamin E, and saponin, from Table 1 were used to model the effect on free testosterone concentration versus the control. As shown in FIG. 1, supplementation of composition in Table 1 over a time period of about 2 days increased the free testosterone concentration to those observed under healthy conditions.

Figure 2:
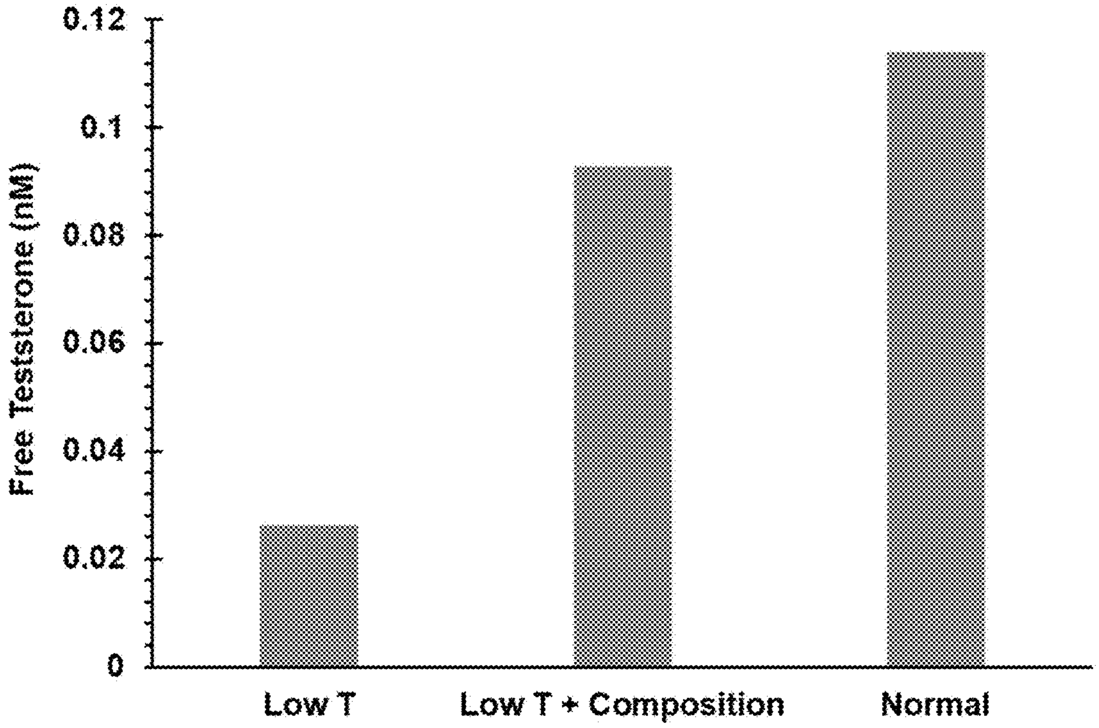
FIG. 2 is a bar graph comparing the steady state concentration of free testosterone levels for normal individuals, individuals with Low T without supplementation of composition described herein, and individuals with supplementation of composition described herein. The plot is based on a biomolecular computational model using CytoSolve® and modeling mechanisms of the testosterone synthesis, testosterone degradation, and oxidative stress. The results show that for healthy individuals, the free testosterone levels are 0.11 nM, whereas for individuals with Low T, the free testosterone levels fall to 0.026 nM. Supplementation of combination of ingredients in composition described herein leads to increase in free testosterone levels to 0.092, which is close to those found in healthy individuals.

FIG. 2 was derived using CytoSolve® to model mechanisms testosterone metabolism in the leydig cells of the testes. The results in FIG. 2 represent the steady state concentrations of testosterone. Under control conditions (Low T), the concentrations of free testosterone were estimated to be 0.026 nM. Supplementation composition as described in Table 1 over a period of two days led to free testosterone concentration of 0.093 nM, which is comparable to the free testosterone level estimated for healthy conditions of 0.11 nM.

Example 2. In Vitro Efficacy Testing of Compositions for Improving Low T Levels Protocol The in vitro efficacy testing of compositions for improving Low T levels on free testosterone concentration are being conducted using TM3 Leydig cell culture model as described in Leisegang et al., 2018 (see, e.g., Leisegang et al. *Reprod Biol Endocrinol* 16, 26, which is incorporated by reference herein in its entirety). Experiments are being conducted with and without the application of the composition described herein. Testosterone concentrations will be measured in the cell culture as an indicator of Low T. Samples from cell culture can be withdrawn and tested for free testosterone concentration using "equilibrium dialysis" technique (see, for example, Bekaert et al. *Endocrine.* 2015 Mar. 13, 50(1): 202-211; Patel et al. *Fertil. Steril.* 2010 November; 94(6): 2161-2166; and Dhindsa et al. *Diabetes Care.* 2011 August; 34(8): 1854-1859; each of which are incorporated by reference herein in their entireties).

Expected Results

Comparison of free testosterone concentration levels in the cell culture with and without application of composition described herein will be performed to determine the efficacy of the composition in improving Low T.

Example 3. Clinical Efficacy Testing of Joint Health Composition on Pain and Inflammation Protocol Clinical efficacy studies are being conducted for the composition described herein using up to 100 subjects over a period of four (4) week. The clinical study protocol is described below.

Study Group Selection

1. Inclusion Criteria
    - a. Age group: Adult population in the age group of ≥45 y
    - b. Gender: Male
    - c. Individual with free testosterone <250 ng/dL or 0.03 nM
    - d. Individuals that reported symptoms and had objective evidence of
        - i. Diminished libido as indicated by a score ≤20 on the Derogatis Inventory of Sexual Function questionnaire (see, for example, Wang et al. 2002*; The Journal of Sexual Medicine;* 15(7): 997-1009; incorporated by reference herein in their entireties)
        - ii. Diminished vitality as indicated by a score <40 on the Functional Assessment of Chronic Illness Therapy (FACIT)-Fatigue Scale (see, for example, Cella et al. 2002; 94:528-538; incorporated by reference herein in their entireties)
2. Exclusion criteria:
    - a. Individuals with chronic illness
    - b. Individuals receiving prescription medication
    - c. Individuals taking other Low T enhancing supplements Study Type Selection Placebo-controlled Randomized clinical study: Random allocation to either the group receiving the supplement under investigation or to a group receiving placebo treatment as the control Study Design Type Parallel-group: Each participant is randomly assigned to a group, and all the participants in the group receive (or do not receive) composition described herein.

Outcome Measurements

1. Will be based on libido and vitality scores
2. Will include primary outcome and secondary outcome
3. Can be self-monitored questionnaire (or a smartphone app) or reported by people who know the individual participating in the study Results Results obtained from the clinical study will be analyzed to determine efficacy of composition described herein using the following steps:

1. Perform appropriate statistical tests to estimate the change levels in the 95% confidence interval for the two study groups where the outcome measure is in the form of ordinal level scale. Examples of such test include:
   a. Wilcoxson Rank-Sum test
   b. Mann-Whiney U test
2. Perform an intention-to-treat (ITT) analysis to overcome the issue arising from dropouts i.e. "Attrition bias."

Other Embodiments

It is to be understood that while the invention has been described in conjunction with the detailed description thereof, the foregoing description is intended to illustrate and not limit the scope of the invention which is defined by the scope of the appended claims. Other aspects, advantages, and modification are within the scope of the following claims.

What is claimed is:

1. A composition comprising:

zinc present in an amount of about 9.1% w/w of the composition;

caffeic acid present in an amount of about 4.7% w/w of the composition;

vitamin C present in an amount of about 4.6% w/w of the composition;

quercetin present in an amount of about 5.9% w/w of the composition;

rutin present in an amount of about 2.9% w/w of the composition;

apigenin present in an amount of about 0.7% w/w of the composition;

icariin present in an amount of about 1.3% w/w of the composition;

kaempferol present in an amount of about 0.1% w/w of the composition;

epicatechin present in an amount of about 0.3% w/w of the composition;

EGCG present in an amount of about 8% w/w of the composition;

gamma oryzanol present in an amount of about 21.7% w/w of the composition;

D-aspartic acid present in an amount of about 21.7% w/w of the composition;

vitamin E present in an amount of about 11.6% w/w of the composition; and, a glycoside selected from the group consisting of ligustroside and ginsenoside Rg1 present in an amount of about 7.4% w/w of the composition.

2. The composition of claim 1 wherein the composition further comprises one or more excipients, diluents, or carriers.

3. A method for improving low testosterone levels of a subject comprising administering to the subject the composition of claim 1.

* * * * *